(12) United States Patent
Rentschler et al.

(10) Patent No.: US 10,335,024 B2
(45) Date of Patent: Jul. 2, 2019

(54) MEDICAL INFLATION, ATTACHMENT AND DELIVERY DEVICES AND RELATED METHODS

(71) Applicant: Board of Regents of the University of Nebraska, Lincoln, NE (US)

(72) Inventors: Mark Rentschler, Boulder, CO (US); Shane Farritor, Lincoln, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 207 days.

(21) Appl. No.: 15/018,530

(22) Filed: Feb. 8, 2016

(65) Prior Publication Data

US 2016/0157709 A1    Jun. 9, 2016

Related U.S. Application Data

(63) Continuation of application No. 12/192,663, filed on Aug. 15, 2008, now abandoned.
(Continued)

(51) Int. Cl.
*A61M 29/00*       (2006.01)
*A61B 1/313*       (2006.01)
(Continued)

(52) U.S. Cl.
CPC ........ *A61B 1/3132* (2013.01); *A61B 17/0218* (2013.01); *A61B 17/0281* (2013.01);
(Continued)

(58) Field of Classification Search
CPC ............ A61B 17/0281; A61B 17/0218; A61B 2017/00283; A61B 2019/2215; A61B 2017/00557; A61B 2017/0042; A61B 1/32; A61B 2017/00876; A61B 2017/00345; A61B 19/26; A61B 2019/2253; A61B 2019/2249; A61B 2017/00292; A61B 2017/00349; A61M 29/02
USPC ........ 606/108, 191, 198, 200, 192; 600/123, 600/139, 37, 204–209; 623/1.11, 1.12; 604/528–532
See application file for complete search history.

(56) References Cited

U.S. PATENT DOCUMENTS 3,870,264 A    3/1975   Robinson
3,989,952 A    11/1976  Timberlake et al.
(Continued)

FOREIGN PATENT DOCUMENTS

CN    1082821918    12/2012
DE    102010040405   3/2012
(Continued)

OTHER PUBLICATIONS

International Preliminary Report on Patentability from related case PCT/US2007/014567, dated Jan. 8, 2009, 11 pp.
(Continued)

*Primary Examiner* — Amy R Weisberg
(74) *Attorney, Agent, or Firm* — Davis, Brown, Koehn, Shors & Roberts, P.C.; Sean D. Solberg

(57) ABSTRACT

The various embodiments disclosed herein relate to procedural space maintenance devices, medical device positioning devices, and devices that provide both procedural space maintenance and device positioning. Further embodiments relate to medical device insertion and/or retraction devices.

20 Claims, 16 Drawing Sheets

Related U.S. Application Data

(60) Provisional application No. 60/956,032, filed on Aug. 15, 2007, provisional application No. 60/990,062, filed on Nov. 26, 2007, provisional application No. 60/990,470, filed on Nov. 27, 2007.

(51) Int. Cl.

| | | |
|---|---|---|
| *A61B 17/02* | (2006.01) | |
| *A61B 34/00* | (2016.01) | |
| *A61B 17/34* | (2006.01) | |
| *A61B 1/32* | (2006.01) | |
| *A61B 17/00* | (2006.01) | |
| *A61B 34/30* | (2016.01) | |
| *A61B 90/50* | (2016.01) | |

(52) U.S. Cl.
CPC .......... *A61B 17/3468* (2013.01); *A61B 34/30* (2016.02); *A61B 34/72* (2016.02); *A61B 34/73* (2016.02); *A61B 1/32* (2013.01); *A61B 90/50* (2016.02); *A61B 2017/0042* (2013.01); *A61B 2017/00283* (2013.01); *A61B 2017/00292* (2013.01); *A61B 2017/00345* (2013.01); *A61B 2017/00349* (2013.01); *A61B 2017/00557* (2013.01); *A61B 2017/00876* (2013.01); *A61B 2017/0225* (2013.01); *A61B 2034/301* (2016.02); *A61B 2034/302* (2016.02)

(56) References Cited

U.S. PATENT DOCUMENTS

| | | |
|---|---|---|
| 4,246,661 A | 1/1981 | Pinson |
| 4,258,716 A | 3/1981 | Sutherland |
| 4,278,077 A | 7/1981 | Mizumoto |
| 4,538,594 A | 9/1985 | Boebel et al. |
| 4,568,311 A | 2/1986 | Miyaki |
| 4,623,183 A | 11/1986 | Amori |
| 4,736,645 A | 4/1988 | Zimmer |
| 4,771,652 A | 9/1988 | Zimmer |
| 4,852,391 A | 8/1989 | Ruch et al. |
| 4,896,015 A | 1/1990 | Taboada et al. |
| 4,897,014 A | 1/1990 | Tietze |
| 4,922,755 A | 5/1990 | Oshiro et al. |
| 4,922,782 A | 5/1990 | Kawai |
| 4,990,050 A | 2/1991 | Tsuge et al. |
| 5,019,968 A | 5/1991 | Wang et al. |
| 5,108,140 A | 4/1992 | Bartholet |
| 5,172,639 A | 12/1992 | Wiesman et al. |
| 5,176,649 A | 1/1993 | Wakabayashi |
| 5,178,032 A | 1/1993 | Zona et al. |
| 5,187,032 A | 2/1993 | Sasaki et al. |
| 5,187,796 A | 2/1993 | Wang et al. |
| 5,195,388 A | 3/1993 | Zona et al. |
| 5,201,325 A | 4/1993 | McEwen et al. |
| 5,217,003 A | 6/1993 | Wilk |
| 5,263,382 A | 11/1993 | Brooks et al. |
| 5,271,384 A | 12/1993 | McEwen et al. |
| 5,284,096 A | 2/1994 | Pelrine et al. |
| 5,297,443 A | 3/1994 | Wentz |
| 5,297,536 A | 3/1994 | Wilk |
| 5,304,899 A | 4/1994 | Sasaki et al. |
| 5,307,447 A | 4/1994 | Asano et al. |
| 5,353,807 A | 10/1994 | DeMarco |
| 5,363,935 A | 11/1994 | Schempf et al. |
| 5,382,885 A | 1/1995 | Salcudean et al. |
| 5,388,528 A | 2/1995 | Pelrine et al. |
| 5,411,550 A * | 5/1995 | Herweck ............... A61F 2/06 600/36 |
| 5,436,542 A | 7/1995 | Petelin et al. |
| 5,441,494 A | 8/1995 | Ortiz |
| 5,458,131 A | 10/1995 | Wilk |
| 5,458,583 A | 10/1995 | McNeely et al. |
| 5,458,598 A | 10/1995 | Feinberg et al. |
| 5,471,515 A | 11/1995 | Fossum et al. |
| 5,515,478 A | 5/1996 | Wang |
| 5,524,180 A | 6/1996 | Wang et al. |
| 5,553,198 A | 9/1996 | Wang et al. |
| 5,562,448 A | 10/1996 | Mushabac |
| 5,588,442 A | 12/1996 | Scovil et al. |
| 5,620,417 A | 4/1997 | Jang et al. |
| 5,623,582 A | 4/1997 | Rosenberg |
| 5,624,380 A | 4/1997 | Shuichi et al. |
| 5,624,398 A | 4/1997 | Smith et al. |
| 5,632,761 A | 5/1997 | Smith et al. |
| 5,645,520 A | 7/1997 | Nakamura et al. |
| 5,657,429 A | 8/1997 | Wang et al. |
| 5,657,584 A | 8/1997 | Hamlin |
| 5,672,168 A | 9/1997 | de la Torre et al. |
| 5,674,030 A | 10/1997 | Sigel |
| 5,728,599 A | 3/1998 | Rosteker et al. |
| 5,736,821 A | 4/1998 | Suyama et al. |
| 5,754,741 A | 5/1998 | Wang et al. |
| 5,762,458 A | 6/1998 | Wang et al. |
| 5,769,640 A | 6/1998 | Jacobus et al. |
| 5,791,231 A | 8/1998 | Cohn et al. |
| 5,792,135 A | 8/1998 | Madhani et al. |
| 5,797,538 A | 8/1998 | Heaton et al. |
| 5,797,900 A | 8/1998 | Madhani et al. |
| 5,807,377 A | 9/1998 | Madhani et al. |
| 5,808,665 A | 9/1998 | Green |
| 5,815,640 A | 9/1998 | Wang et al. |
| 5,825,982 A | 10/1998 | Wright et al. |
| 5,841,950 A | 11/1998 | Wang et al. |
| 5,845,646 A | 12/1998 | Lemelson |
| 5,855,583 A | 1/1999 | Wang et al. |
| 5,876,325 A | 3/1999 | Mizuno et al. |
| 5,878,193 A | 3/1999 | Wang et al. |
| 5,878,783 A | 3/1999 | Smart |
| 5,895,417 A * | 4/1999 | Pomeranz ........ A61B 17/00234 606/41 |
| 5,906,591 A | 5/1999 | Dario et al. |
| 5,907,664 A | 5/1999 | Wang et al. |
| 5,910,129 A | 6/1999 | Koblish et al. |
| 5,911,036 A | 6/1999 | Wright et al. |
| 5,971,976 A | 10/1999 | Wang et al. |
| 5,993,467 A | 11/1999 | Yoon |
| 6,001,108 A | 12/1999 | Wang et al. |
| 6,007,550 A | 12/1999 | Wang et al. |
| 6,030,365 A | 2/2000 | Laufer |
| 6,031,371 A | 2/2000 | Smart |
| 6,058,323 A | 5/2000 | Lemelson |
| 6,063,095 A | 5/2000 | Wang et al. |
| 6,066,090 A | 5/2000 | Yoon |
| 6,102,850 A | 8/2000 | Wang et al. |
| 6,107,795 A | 8/2000 | Smart |
| 6,132,368 A | 10/2000 | Cooper |
| 6,132,441 A | 10/2000 | Grace |
| 6,139,563 A | 10/2000 | Cosgrove, III et al. |
| 6,156,006 A | 12/2000 | Brosens et al. |
| 6,159,146 A | 12/2000 | El Gazayerli |
| 6,162,171 A | 12/2000 | Ng et al. |
| D438,617 S | 3/2001 | Cooper et al. |
| 6,206,903 B1 | 3/2001 | Ramans |
| D441,076 S | 4/2001 | Cooper et al. |
| 6,223,100 B1 | 4/2001 | Green |
| D441,862 S | 5/2001 | Cooper et al. |
| 6,238,415 B1 | 5/2001 | Sepetka et al. |
| 6,240,312 B1 | 5/2001 | Alfano et al. |
| 6,241,730 B1 | 6/2001 | Alby |
| 6,244,809 B1 | 6/2001 | Wang et al. |
| 6,246,200 B1 | 6/2001 | Blumenkranz et al. |
| D444,555 S | 7/2001 | Cooper et al. |
| 6,286,514 B1 | 9/2001 | Lemelson |
| 6,292,678 B1 | 9/2001 | Hall et al. |
| 6,293,282 B1 | 9/2001 | Lemelson |
| 6,296,635 B1 | 10/2001 | Smith et al. |
| 6,309,397 B1 | 10/2001 | Julian et al. |
| 6,309,403 B1 | 10/2001 | Minaret et al. |
| 6,312,435 B1 | 11/2001 | Wallace et al. |
| 6,321,106 B1 | 11/2001 | Lemelson |
| 6,327,492 B1 | 12/2001 | Lemelson |
| 6,331,181 B1 | 12/2001 | Tiemey et al. |
| 6,346,072 B1 | 2/2002 | Cooper |

(56) References Cited

U.S. PATENT DOCUMENTS

| | | |
|---|---|---|
| 6,352,503 B1 | 3/2002 | Matsui et al. |
| 6,364,888 B1 | 4/2002 | Niemeyer et al. |
| 6,371,952 B1 | 4/2002 | Madhani et al. |
| 6,394,998 B1 | 5/2002 | Wallace et al. |
| 6,398,726 B1 | 6/2002 | Ramans et al. |
| 6,400,980 B1 | 6/2002 | Lemelson |
| 6,408,224 B1 | 6/2002 | Lemelson |
| 6,424,885 B1 | 7/2002 | Niemeyer et al. |
| 6,432,112 B2 | 8/2002 | Brock et al. |
| 6,436,107 B1 | 8/2002 | Wang et al. |
| 6,441,577 B2 | 8/2002 | Blumenkranz et al. |
| 6,450,104 B1 | 9/2002 | Grant et al. |
| 6,451,027 B1 | 9/2002 | Cooper et al. |
| 6,454,758 B1 | 9/2002 | Thompson et al. |
| 6,459,926 B1 | 10/2002 | Nowlin et al. |
| 6,463,361 B1 | 10/2002 | Wang et al. |
| 6,468,203 B2 | 10/2002 | Belson |
| 6,468,265 B1 | 10/2002 | Evans et al. |
| 6,470,236 B2 | 10/2002 | Ohtsuki |
| 6,491,691 B1 | 12/2002 | Morley et al. |
| 6,491,701 B2 | 12/2002 | Nemeyer et al. |
| 6,493,608 B1 | 12/2002 | Niemeyer et al. |
| 6,496,099 B2 | 12/2002 | Wang et al. |
| 6,508,413 B2 | 1/2003 | Bauer et al. |
| 6,512,345 B2 | 1/2003 | Borenstein |
| 6,522,906 B1 | 2/2003 | Salisbury, Jr. et al. |
| 6,544,276 B1 | 4/2003 | Azizi |
| 6,548,982 B1 | 4/2003 | Papanikolopoulos et al. |
| 6,554,790 B1 | 4/2003 | Moll |
| 6,565,554 B1 | 5/2003 | Niemeyer |
| 6,574,355 B2 | 6/2003 | Green |
| 6,587,750 B2 | 7/2003 | Gerbi et al. |
| 6,591,239 B1 | 7/2003 | McCall et al. |
| 6,594,552 B1 | 7/2003 | Nowlin et al. |
| 6,610,007 B2 | 8/2003 | Belson et al. |
| 6,620,173 B2 | 9/2003 | Gerbi et al. |
| 6,642,836 B1 | 11/2003 | Wang et al. |
| 6,645,196 B1 | 11/2003 | Nixon et al. |
| 6,646,541 B1 | 11/2003 | Wang et al. |
| 6,648,814 B2 | 11/2003 | Kim et al. |
| 6,659,939 B2 | 12/2003 | Moll et al. |
| 6,661,571 B1 | 12/2003 | Shioda et al. |
| 6,671,581 B2 | 12/2003 | Niemeyer et al. |
| 6,676,684 B1 | 1/2004 | Morley et al. |
| 6,684,129 B2 | 1/2004 | Salisbury, Jr. et al. |
| 6,685,648 B2 | 2/2004 | Flaherty et al. |
| 6,685,698 B2 | 2/2004 | Morley et al. |
| 6,687,571 B1 | 2/2004 | Byme et al. |
| 6,692,485 B1 | 2/2004 | Brock et al. |
| 6,699,177 B1 | 3/2004 | Wang et al. |
| 6,699,235 B2 | 3/2004 | Wallace et al. |
| 6,702,734 B2 | 3/2004 | Kim et al. |
| 6,702,805 B1 | 3/2004 | Stuart |
| 6,714,839 B2 | 3/2004 | Salisbury, Jr. et al. |
| 6,714,841 B1 | 3/2004 | Wright et al. |
| 6,719,684 B2 | 4/2004 | Kim et al. |
| 6,720,988 B1 | 4/2004 | Gere et al. |
| 6,726,699 B1 | 4/2004 | Wright et al. |
| 6,728,599 B2 | 4/2004 | Wright et al. |
| 6,730,021 B2 | 5/2004 | Vassiliades, Jr. et al. |
| 6,731,988 B1 | 5/2004 | Green |
| 6,746,443 B1 | 6/2004 | Morley et al. |
| 6,764,441 B2 | 7/2004 | Chiel et al. |
| 6,764,445 B2 | 7/2004 | Ramans et al. |
| 6,766,204 B2 | 7/2004 | Niemeyer et al. |
| 6,770,081 B1 | 8/2004 | Cooper et al. |
| 6,774,597 B1 | 8/2004 | Borenstein |
| 6,776,165 B2 | 8/2004 | Jin |
| 6,780,184 B2 | 8/2004 | Tanrisever |
| 6,783,524 B2 | 8/2004 | Anderson et al. |
| 6,785,593 B2 | 8/2004 | Wang et al. |
| 6,788,018 B1 | 9/2004 | Blumenkranz |
| 6,792,663 B2 | 9/2004 | Krzyzanowski |
| 6,793,653 B2 | 9/2004 | Sanchez et al. |
| 6,799,065 B1 | 9/2004 | Niemeyer |
| 6,799,088 B2 | 9/2004 | Wang et al. |
| 6,801,325 B2 | 10/2004 | Farr et al. |
| 6,804,581 B2 | 10/2004 | Wang et al. |
| 6,810,281 B2 | 10/2004 | Brock et al. |
| 6,817,972 B2 | 11/2004 | Snow |
| 6,817,974 B2 | 11/2004 | Cooper et al. |
| 6,817,975 B1 | 11/2004 | Farr et al. |
| 6,820,653 B1 | 11/2004 | Schempf et al. |
| 6,824,508 B2 | 11/2004 | Kim et al. |
| 6,824,510 B2 | 11/2004 | Kim et al. |
| 6,832,988 B2 | 12/2004 | Sprout |
| 6,832,996 B2 | 12/2004 | Woloszko et al. |
| 6,836,703 B2 | 12/2004 | Wang et al. |
| 6,837,846 B2 | 1/2005 | Jaffe et al. |
| 6,837,883 B2 | 1/2005 | Moll et al. |
| 6,839,612 B2 | 1/2005 | Sanchez et al. |
| 6,840,938 B1 | 1/2005 | Morley et al. |
| 6,852,107 B2 | 2/2005 | Wang et al. |
| 6,858,003 B2 | 2/2005 | Evans et al. |
| 6,860,346 B2 | 3/2005 | Burt et al. |
| 6,860,877 B1 | 3/2005 | Sanchez et al. |
| 6,866,671 B2 | 3/2005 | Tiemey et al. |
| 6,870,343 B2 | 3/2005 | Borenstein et al. |
| 6,871,117 B2 | 3/2005 | Wang et al. |
| 6,871,563 B2 | 3/2005 | Choset et al. |
| 6,879,880 B2 | 4/2005 | Nowlin et al. |
| 6,892,112 B2 | 5/2005 | Wang et al. |
| 6,899,705 B2 | 5/2005 | Niemeyer |
| 6,902,560 B1 | 6/2005 | Morley et al. |
| 6,905,460 B2 | 6/2005 | Wang et al. |
| 6,905,491 B1 | 6/2005 | Wang et al. |
| 6,911,916 B1 | 6/2005 | Wang et al. |
| 6,917,176 B2 | 7/2005 | Schempf et al. |
| 6,933,695 B2 | 8/2005 | Blumenkranz |
| 6,936,001 B1 | 8/2005 | Snow |
| 6,936,003 B2 | 8/2005 | Iddan |
| 6,936,042 B2 | 8/2005 | Wallace et al. |
| 6,943,663 B2 | 9/2005 | Wang et al. |
| 6,949,096 B2 | 9/2005 | Davison et al. |
| 6,951,535 B2 | 10/2005 | Ghodoussi et al. |
| 6,965,812 B2 | 11/2005 | Wang et al. |
| 6,974,411 B2 | 12/2005 | Belson |
| 6,974,449 B2 | 12/2005 | Niemeyer |
| 6,979,423 B2 | 12/2005 | Moll |
| 6,984,203 B2 | 1/2006 | Tartaglia et al. |
| 6,984,205 B2 | 1/2006 | Gazdzinski |
| 6,991,627 B2 | 1/2006 | Madhani et al. |
| 6,993,413 B2 | 1/2006 | Sunaoshi |
| 6,994,703 B2 | 2/2006 | Wang et al. |
| 6,994,708 B2 | 2/2006 | Manzo |
| 6,997,908 B2 | 2/2006 | Carrillo, Jr. et al. |
| 7,025,064 B2 | 4/2006 | Wang et al. |
| 7,027,892 B2 | 4/2006 | Wang et al. |
| 7,033,344 B2 | 4/2006 | Imran |
| 7,039,453 B2 | 5/2006 | Mullick |
| 7,042,184 B2 | 5/2006 | Oleynikov et al. |
| 7,048,745 B2 | 5/2006 | Tierney et al. |
| 7,053,752 B2 | 5/2006 | Wang et al. |
| 7,063,682 B1 | 6/2006 | Whayne et al. |
| 7,066,879 B2 | 6/2006 | Fowler et al. |
| 7,066,926 B2 | 6/2006 | Wallace et al. |
| 7,074,179 B2 | 7/2006 | Wang et al. |
| 7,077,446 B2 | 7/2006 | Kameda et al. |
| 7,083,571 B2 | 8/2006 | Wang et al. |
| 7,083,615 B2 | 8/2006 | Peterson et al. |
| 7,087,049 B2 | 8/2006 | Nowlin et al. |
| 7,090,683 B2 | 8/2006 | Brock et al. |
| 7,097,640 B2 | 8/2006 | Wang et al. |
| 7,105,000 B2 | 9/2006 | McBrayer |
| 7,107,090 B2 | 9/2006 | Salisbury, Jr. et al. |
| 7,109,678 B2 | 9/2006 | Kraus et al. |
| 7,118,582 B1 | 10/2006 | Wang et al. |
| 7,121,781 B2 | 10/2006 | Sanchez et al. |
| 7,125,403 B2 | 10/2006 | Julian et al. |
| 7,126,303 B2 | 10/2006 | Farritor et al. |
| 7,147,650 B2 | 12/2006 | Lee |
| 7,155,315 B2 | 12/2006 | Niemeyer et al. |
| 7,169,141 B2 | 1/2007 | Brock et al. |
| 7,182,025 B2 | 2/2007 | Ghorbel et al. |

(56) References Cited

U.S. PATENT DOCUMENTS

| | | |
|---|---|---|
| 7,182,089 B2 | 2/2007 | Ries |
| 7,199,545 B2 | 4/2007 | Oleynikov et al. |
| 7,206,626 B2 | 4/2007 | Quaid, III |
| 7,206,627 B2 | 4/2007 | Abovitz et al. |
| 7,210,364 B2 | 5/2007 | Ghorbel et al. |
| 7,214,230 B2 | 5/2007 | Brock et al. |
| 7,217,240 B2 | 5/2007 | Snow |
| 7,239,940 B2 | 7/2007 | Wang et al. |
| 7,250,028 B2 | 7/2007 | Julian et al. |
| 7,259,652 B2 | 8/2007 | Wang et al. |
| 7,273,488 B2 | 9/2007 | Nakamura et al. |
| 7,311,107 B2 | 12/2007 | Harel et al. |
| 7,339,341 B2 | 3/2008 | Oleynikov et al. |
| 7,372,229 B2 | 5/2008 | Farritor et al. |
| 7,447,537 B1 | 11/2008 | Funda et al. |
| 7,492,116 B2 | 2/2009 | Oleynikov et al. |
| 7,566,300 B2 | 7/2009 | Devierre et al. |
| 7,574,250 B2 | 8/2009 | Niemeyer |
| 7,637,905 B2 | 12/2009 | Saadat et al. |
| 7,645,230 B2 | 1/2010 | Mikkaichi et al. |
| 7,655,004 B2 | 2/2010 | Long |
| 7,670,329 B2 | 3/2010 | Flaherty et al. |
| 7,731,727 B2 | 6/2010 | Sauer |
| 7,762,825 B2 | 7/2010 | Burbank et al. |
| 7,772,796 B2 | 8/2010 | Farritor et al. |
| 7,785,251 B2 | 8/2010 | Wilk |
| 7,785,333 B2 | 8/2010 | Miyamoto et al. |
| 7,789,825 B2 | 9/2010 | Nobis et al. |
| 7,794,494 B2 | 9/2010 | Sahatjian et al. |
| 7,865,266 B2 | 1/2011 | Moll et al. |
| 7,960,935 B2 | 6/2011 | Farritor et al. |
| 8,021,358 B2 | 9/2011 | Doyle et al. |
| 8,179,073 B2 | 5/2012 | Farritor et al. |
| 8,353,897 B2 | 1/2013 | Doyle et al. |
| 9,089,353 B2 | 7/2015 | Farritor |
| 2001/0018591 A1 | 8/2001 | Brock et al. |
| 2001/0049497 A1 | 12/2001 | Kalloo et al. |
| 2002/0003173 A1 | 1/2002 | Bauer et al. |
| 2002/0013601 A1 | 1/2002 | Nobles et al. |
| 2002/0026186 A1 | 2/2002 | Woloszka et al. |
| 2002/0038077 A1 | 3/2002 | de la Torre et al. |
| 2002/0065507 A1 | 5/2002 | Azizi |
| 2002/0091374 A1 | 7/2002 | Cooper |
| 2002/0103417 A1 | 8/2002 | Gazdzinski |
| 2002/0111535 A1 | 8/2002 | Kim et al. |
| 2002/0120254 A1 | 8/2002 | Julien et al. |
| 2002/0128552 A1 | 9/2002 | Nowlin et al. |
| 2002/0140392 A1 | 10/2002 | Borenstein et al. |
| 2002/0147487 A1 | 10/2002 | Sundquist et al. |
| 2002/0151906 A1 | 10/2002 | Demarais et al. |
| 2002/0156347 A1 | 10/2002 | Kim et al. |
| 2002/0171385 A1 | 11/2002 | Kim et al. |
| 2002/0173700 A1 | 11/2002 | Kim et al. |
| 2002/0190682 A1 | 12/2002 | Schempf et al. |
| 2003/0020810 A1 | 1/2003 | Takizawa et al. |
| 2003/0045888 A1 | 3/2003 | Brock et al. |
| 2003/0065250 A1 | 4/2003 | Chiel et al. |
| 2003/0089267 A1 | 5/2003 | Ghorbel et al. |
| 2003/0092964 A1 | 5/2003 | Kim et al. |
| 2003/0097129 A1 | 5/2003 | Davison et al. |
| 2003/0100817 A1 | 5/2003 | Wang et al. |
| 2003/0114731 A1 | 6/2003 | Cadeddu et al. |
| 2003/0135203 A1 | 7/2003 | Wang et al. |
| 2003/0139742 A1 | 7/2003 | Wampler et al. |
| 2003/0144656 A1 | 7/2003 | Ocel et al. |
| 2003/0167000 A1 | 9/2003 | Mullick |
| 2003/0172871 A1 | 9/2003 | Scherer |
| 2003/0179308 A1 | 9/2003 | Zamorano et al. |
| 2003/0181788 A1 | 9/2003 | Yokoi et al. |
| 2003/0229268 A1 | 12/2003 | Uchiyama et al. |
| 2003/0230372 A1 | 12/2003 | Schmidt |
| 2004/0117032 A1 | 1/2004 | Roth et al. |
| 2004/0024311 A1 | 2/2004 | Quaid |
| 2004/0034282 A1 | 2/2004 | Quaid |
| 2004/0034283 A1 | 2/2004 | Quaid |
| 2004/0034302 A1 | 2/2004 | Abovitz et al. |
| 2004/0050394 A1 | 3/2004 | Jin |
| 2004/0070822 A1 | 4/2004 | Shioda et al. |
| 2004/0099175 A1 | 5/2004 | Perrot et al. |
| 2004/0102772 A1 | 5/2004 | Baxter et al. |
| 2004/0106916 A1 | 6/2004 | Quaid et al. |
| 2004/0111113 A1 | 6/2004 | Nakamura et al. |
| 2004/0138525 A1 | 7/2004 | Saadat |
| 2004/0138552 A1 | 7/2004 | Harel et al. |
| 2004/0140786 A1 | 7/2004 | Borenstein |
| 2004/0153057 A1 | 8/2004 | Davison |
| 2004/0173116 A1 | 9/2004 | Ghorbel et al. |
| 2004/0176664 A1 | 9/2004 | Iddan |
| 2004/0215331 A1 | 10/2004 | Chew et al. |
| 2004/0225229 A1 | 11/2004 | Viola |
| 2004/0254680 A1 | 12/2004 | Sunaoshi |
| 2004/0267326 A1 | 12/2004 | Ocel et al. |
| 2005/0014994 A1 | 1/2005 | Fowler et al. |
| 2005/0021069 A1 | 1/2005 | Feuer et al. |
| 2005/0029978 A1 | 2/2005 | Oleynikov et al. |
| 2005/0043583 A1 | 2/2005 | Killmann et al. |
| 2005/0049462 A1 | 3/2005 | Kanazawa |
| 2005/0054901 A1 | 3/2005 | Yoshino |
| 2005/0054902 A1 | 3/2005 | Konno |
| 2005/0064378 A1 | 3/2005 | Toly |
| 2005/0065400 A1 | 3/2005 | Banik et al. |
| 2005/0083460 A1 | 4/2005 | Hattori et al. |
| 2005/0095650 A1 | 5/2005 | Khalili et al. |
| 2005/0096502 A1 | 5/2005 | Khalili |
| 2005/0143644 A1 | 6/2005 | Gilad et al. |
| 2005/0154376 A1 | 7/2005 | Riviere et al. |
| 2005/0165449 A1 | 7/2005 | Cadeddu et al. |
| 2005/0283137 A1 | 12/2005 | Doyle et al. |
| 2005/0288555 A1 | 12/2005 | Binmoeller |
| 2005/0288665 A1 | 12/2005 | Woloszko |
| 2006/0020272 A1 | 1/2006 | Gildenberg |
| 2006/0046226 A1 | 3/2006 | Bergler et al. |
| 2006/0119304 A1 | 6/2006 | Farritor et al. |
| 2006/0149135 A1 | 7/2006 | Paz |
| 2006/0152591 A1 | 7/2006 | Lin |
| 2006/0155263 A1 | 7/2006 | Lipow |
| 2006/0195015 A1 | 8/2006 | Mullick et al. |
| 2006/0196301 A1 | 9/2006 | Oleynikov et al. |
| 2006/0198619 A1 | 9/2006 | Oleynikov et al. |
| 2006/0241570 A1 | 10/2006 | Wilk |
| 2006/0241732 A1 | 10/2006 | Denker |
| 2006/0253109 A1 | 11/2006 | Chu |
| 2006/0258954 A1 | 11/2006 | Timberlake et al. |
| 2007/0032701 A1 | 2/2007 | Fowler et al. |
| 2007/0043397 A1 | 2/2007 | Ocel et al. |
| 2007/0055342 A1 | 3/2007 | Wu et al. |
| 2007/0080658 A1 | 4/2007 | Farritor et al. |
| 2007/0106113 A1 | 5/2007 | Ravo |
| 2007/0123748 A1 | 5/2007 | Meglan |
| 2007/0142725 A1 | 6/2007 | Hardin et al. |
| 2007/0156019 A1 | 7/2007 | Larkin et al. |
| 2007/0156211 A1 | 7/2007 | Ferren et al. |
| 2007/0167955 A1 | 7/2007 | De La Menardiere et al. |
| 2007/0225633 A1 | 9/2007 | Ferren et al. |
| 2007/0225634 A1 | 9/2007 | Ferren et al. |
| 2007/0241714 A1 | 10/2007 | Okeynikov et al. |
| 2007/0244520 A1 | 10/2007 | Ferren et al. |
| 2007/0250064 A1 | 10/2007 | Darois et al. |
| 2007/0255273 A1 | 11/2007 | Fernandez et al. |
| 2008/0004634 A1 | 1/2008 | Farritor et al. |
| 2008/0015565 A1 | 1/2008 | Davison |
| 2008/0015566 A1 | 1/2008 | Livneh |
| 2008/0033569 A1 | 2/2008 | Ferren et al. |
| 2008/0045803 A1 | 2/2008 | Williams |
| 2008/0058835 A1 | 3/2008 | Farritor et al. |
| 2008/0058989 A1 | 3/2008 | Oleynikov et al. |
| 2008/0103440 A1 | 5/2008 | Ferren et al. |
| 2008/0109014 A1 | 5/2008 | de la Pena |
| 2008/0111513 A1 | 5/2008 | Farritor et al. |
| 2008/0119870 A1 | 5/2008 | Williams et al. |
| 2008/0132890 A1 | 6/2008 | Woloszko et al. |
| 2008/0161804 A1 | 7/2008 | Rioux et al. |
| 2008/0164079 A1 | 7/2008 | Ferren et al. |
| 2008/0183033 A1 | 7/2008 | Bern et al. |

(56) References Cited

U.S. PATENT DOCUMENTS

| | | |
|---|---|---|
| 2008/0221591 A1 | 9/2008 | Farritor et al. |
| 2008/0269557 A1 | 10/2008 | Marescaux et al. |
| 2008/0269562 A1 | 10/2008 | Marescaux et al. |
| 2009/0020724 A1 | 1/2009 | Paffrath |
| 2009/0024142 A1 | 1/2009 | Ruiz Morales |
| 2009/0048612 A1 | 2/2009 | Farritor et al. |
| 2009/0054909 A1 | 2/2009 | Farritor et al. |
| 2009/0069821 A1 | 3/2009 | Farritor et al. |
| 2009/0076536 A1 | 3/2009 | Rentschler et al. |
| 2009/0137952 A1 | 5/2009 | Ramamurthy et al. |
| 2009/0143787 A9 | 6/2009 | De La Pena |
| 2009/0163929 A1 | 6/2009 | Yeung et al. |
| 2009/0171373 A1 | 7/2009 | Farritor et al. |
| 2009/0234369 A1 | 9/2009 | Bax et al. |
| 2009/0236400 A1 | 9/2009 | Cole et al. |
| 2009/0240246 A1 | 9/2009 | Devill et al. |
| 2009/0247821 A1 | 10/2009 | Rogers |
| 2009/0248038 A1 | 10/2009 | Blumenkranz et al. |
| 2009/0281377 A1 | 11/2009 | Newell et al. |
| 2009/0305210 A1 | 12/2009 | Guru et al. |
| 2010/0010294 A1 | 1/2010 | Conlon et al. |
| 2010/0016659 A1 | 1/2010 | Weitzner et al. |
| 2010/0016853 A1 | 1/2010 | Burbank |
| 2010/0042097 A1 | 2/2010 | Newton et al. |
| 2010/0056863 A1 | 3/2010 | Dejima et al. |
| 2010/0069710 A1 | 3/2010 | Yamatani et al. |
| 2010/0069940 A1 | 3/2010 | Miller et al. |
| 2010/0081875 A1 | 4/2010 | Fowler et al. |
| 2010/0139436 A1 | 6/2010 | Kawashima et al. |
| 2010/0198231 A1 | 8/2010 | Manzo et al. |
| 2010/0204713 A1 | 8/2010 | Ruiz |
| 2010/0245549 A1 | 9/2010 | Allen et al. |
| 2010/0262162 A1 | 10/2010 | Omori |
| 2010/0292691 A1 | 11/2010 | Brogna |
| 2010/0318059 A1 | 12/2010 | Farritor et al. |
| 2011/0015569 A1 | 1/2011 | Kirschenman et al. |
| 2011/0020779 A1 | 1/2011 | Hannaford et al. |
| 2011/0071347 A1 | 3/2011 | Rogers et al. |
| 2011/0071544 A1 | 3/2011 | Steger et al. |
| 2011/0077478 A1 | 3/2011 | Freeman et al. |
| 2011/0098529 A1 | 4/2011 | Ostrovsky et al. |
| 2011/0152615 A1 | 6/2011 | Schostek et al. |
| 2011/0224605 A1 | 9/2011 | Farritor et al. |
| 2011/0230894 A1 | 9/2011 | Simaan et al. |
| 2011/0237890 A1 | 9/2011 | Farritor et al. |
| 2011/0238080 A1 | 9/2011 | Ranjit et al. |
| 2011/0264078 A1 | 10/2011 | Lipow |
| 2011/0270443 A1 | 11/2011 | Kamiya et al. |
| 2012/0035582 A1 | 2/2012 | Nelson et al. |
| 2012/0109150 A1 | 5/2012 | Quaid et al. |
| 2012/0116362 A1 | 5/2012 | Kieturakis |
| 2012/0179168 A1 | 7/2012 | Farritor |
| 2012/0253515 A1 | 10/2012 | Coste-Maniere et al. |
| 2013/0041360 A1 | 2/2013 | Farritor |
| 2013/0131695 A1 | 5/2013 | Scarfogliero et al. |
| 2013/0345717 A1 | 5/2013 | Scarfogliero et al. |
| 2014/0039515 A1 | 2/2014 | Mondry et al. |
| 2014/0046340 A1 | 2/2014 | Wilson et al. |
| 2014/0058205 A1 | 2/2014 | Frederick et al. |
| 2014/0303434 A1 | 10/2014 | Farritor et al. |
| 2015/0051446 A1 | 2/2015 | Farritor et al. |

FOREIGN PATENT DOCUMENTS

| | | |
|---|---|---|
| EP | 1354670 | 10/2003 |
| EP | 2286756 | 2/2011 |
| EP | 2286756 A1 | 2/2011 |
| EP | 2329787 | 8/2011 |
| EP | 2563261 | 3/2013 |
| JP | 2004144533 | 5/1990 |
| JP | 5115425 | 5/1993 |
| JP | 200716235 | 6/1993 |
| JP | 2006507809 | 9/1994 |
| JP | 07 136173 | 5/1995 |
| JP | 7306155 | 11/1995 |
| JP | 08-224248 | 9/1996 |
| JP | 2001500510 | 1/2001 |
| JP | 2001505810 | 5/2001 |
| JP | 2003220065 | 8/2003 |
| JP | 2004322310 | 6/2004 |
| JP | 2004180781 | 7/2004 |
| JP | 2004329292 | 11/2004 |
| JP | 2006508049 | 3/2006 |
| JP | 2009-106606 | 5/2009 |
| JP | 2010-533045 | 10/2010 |
| JP | 2010-536436 | 12/2010 |
| JP | 2011-504794 | 2/2011 |
| JP | 2011-045500 | 3/2011 |
| JP | 2011-115591 | 6/2011 |
| WO | WO 1992/21291 | 5/1991 |
| WO | WO 0189405 | 11/2001 |
| WO | WO 2002/082979 | 10/2002 |
| WO | WO 2002/100256 | 12/2002 |
| WO | WO 2005/009211 | 7/2004 |
| WO | WO 2005044095 | 5/2005 |
| WO | WO 2006/052927 | 8/2005 |
| WO | WO 2006 005075 | 1/2006 |
| WO | WO 2006/079108 | 1/2006 |
| WO | WO2006079108 | 7/2006 |
| WO | WO 2007011654 | 1/2007 |
| WO | WO 2007/111571 | 10/2007 |
| WO | WO 2007/149559 | 12/2007 |
| WO | WO 2009023851 A1 | 8/2008 |
| WO | WO 2009/144729 | 12/2009 |
| WO | WO2010/042611 | 4/2010 |
| WO | WO2010/046823 | 4/2010 |
| WO | WO201050771 A2 | 5/2010 |
| WO | WO 2011/118646 A1 | 9/2011 |
| WO | WO 2011/135503 A1 | 11/2011 |
| WO | WO 2011135503 | 11/2011 |
| WO | WO 2011075693 | 7/2012 |
| WO | WO 2013009887 | 1/2013 |
| WO | WO 2014011238 | 1/2014 |

OTHER PUBLICATIONS

International Search report and Written Opinion from international application No. PCT/US2012/41911, dated Mar. 13, 2013.

International Search Report and Written Opinion from international application No. PCT/US12/46274, dated Sep. 25, 2012.

International Search Report and Written Opinion from international application No. PCT/US2007/089191, dated Nov. 10, 2008, 20 pp.

"International Search Report and Written Opinion from international application No. PCT/US07/14567, dated Apr. 28, 2008, 19 pp."

International Search Report and Written Opinion of international application No. PCT/US2008/069822, dated Aug. 5, 2009, 12 pp.

International Search Report and Written Opinion of international application No. PCT/US2008/073334, dated Jan. 12, 2009, 11 pp.

International Search Report and Written Opinion of international application No. PCT/US2008/073369, dated Nov. 12, 2008, 12 pp.

International Search Report and Written Opinion issued in PCT/US11/46809, dated Dec. 8, 2011.

Ishiyama et al., "Spiral-type Micro-machine for Medical Applications," 2000 International Symposium on Micromechatronics and Human Science, 2000: 65-69.

Jagannath et al., "Peroral transgastric endoscopic ligation of fallopian tubes with long-term survival in a porcine model," Gastrointestinal Endoscopy, 2005; 61(3): 449-453.

Kalloo et al., "Flexible transgastric peritoneoscopy: a novel approach to diagnostic and therapeutic interventions in the peritoneal cavity," Gastrointestinal Endoscopy, 2004; 60(1): 114-117.

Kang et al., "Robotic Assistants Aid Surgeons During Minimally Invasive Procedures," IEEE Engineering in Medicine and Biology, Jan.-Feb. 2001; pp. 94-104.

Kantsevoy et al., "Endoscopic gastrojejunostomy with survival in a porcine model," Gastrointestinal Endoscopy, 2005; 62(2): 287-292.

Kantsevoy et al., "Transgastric endoscopic splenectomy," Surgical Endoscopy, 2006; 20: 522-525.

(56) References Cited

OTHER PUBLICATIONS

Kazemier et al. (1998), "Vascular Injuries During Laparoscopy," J. Am. Coli. Surg. 186(5): 604-5.
Kim, "Early Experience with Telemanipulative Robot-Assisted Laparoscopic Cholecystectomy Using da Vinci," Surgical Laparoscopy, Endoscopy & Percutaneous Techniques, 2002; 12(1):33-40.
Ko et al., "Per-Oral transgastric abdominal surgery," Chinese Journal of Digestive Diseases, 2006; 7: 67-70.
Lafullarde et al., "Laparoscopic Nissen Fundoplication: Five-year Results and Beyond," Arch/Surg, Feb. 2001; 136:180-184.
Leffett et al. (2002), "Aortic injury during laparoscopic fundoplication," Surg. Endoscopy 16(2): 362.
Li et al. (2000), "Microvascular Anastomoses Performed in Rats Using a Microsurgical Telemanipulator," Comp. Aid. Surg. 5: 326-332.
Liem et al., "Comparison of Conventional Anterior Surgery and Laparoscopic Surgery for Inguinal-hernia Repair," New England Journal of Medicine, 1997; 336 (22): 1541-1547.
MacFarlane et al., "Force-Feedback Grasper Helps Restore the Sense of Touch in Minimally Invasive Surgery," Journal of Gastrointestinal Surgery, 1999; 3: 278-285.
Mack et al., "Present Role of Thoracoscopy in the Diagnosis and Treatment of Diseases of the Chest," Ann Thorac Surgery, 1992; 54: 403-409.
Mack, "Minimally Invasive and Robotic Surgery," JAMA, Feb. 2001; 285(5): 568-572.
Mei et al., "Wireless Drive and Control of a Swimming Microrobot," Proceedings of the 2002 IEEE International Conference on Robotics & Automation, May 2002: 1131-1136.
Melvin et al., "Computer-Enhanced vs. Standard Laparoscopic Antireflux Surgery," J Gastrointest Surg 2002; 6: 11-16.
Menciassi et al., "Locomotion of a Leffed Capsule in the Gastrointestinal Tract: Theoretical Study and Preliminary Technological Results," IEEE Int. Conf. on Engineering in Medicine and Biology, San Francisco, CA, pp. 2767-2770, Sep. 2004.
Menciassi et al., "Robotic Solutions and Mechanisms for a Semi-Autonomous Endoscope," Proceedings of the 2002 IEEE/RSJ Intl. Conference on Intelligent Robots and Systems, Oct. 2002; 1379-1384.
Menciassi et al., "Shape memory alloy clamping devices of a capsule for monitoring tasks in the gastrointestinal tract," J. Micromech. Microeng, 2005, 15: 2045-2055.
Meron, "The development of the swallowable video capsule (M2A)," Gastrointestinal Endoscopy 2000; 52 6: 817-819.
Micron, http://www.micron.com, 2006, 1/4-inch VGA NTSC/PAL CMOS Digital Image Sensor, 98 pp.
Midday Jeff et al., "Material Handling System for Robotic natural Orifice Surgery", Proceedings of the 2011 Design of medical Devices Conference, Apr. 12-14, 2011, Minneapolis, MN, 4 pages.
Miller, Ph.D., et al., "In-Vivo Stereoscopic Imaging System with 5 Degrees-of-Freedom for Minimal Access Surgery," Dept. of Computer Science and Dept. of Surgery, Columbia University, New York, NY, 7 pp.
Munro (2002), "Laparoscopic access: complications, technologies, and techniques," Curro Opin. Obstet. Gynecol., 14(4): 365-74.
Nio et al., "Efficiency of manual vs robotical (Zeus) assisted laparoscopic surgery in the performance of standardized tasks," Surg Endosc, 2002; 16: 412-415.
Office Action dated Apr. 17, 2007, received in related case U.S. Appl. No. 11/552,379, 5 pp.
Office Action dated Apr. 3, 2009, received in related case U.S. Appl. No. 11/932,516, 43 pp.
Office Action dated Aug. 18, 2006, received in related case U.S. Appl. No. 11/398,174, 6 pp.
Office Action dated Aug. 21, 2006, received in related case U.S. Appl. No. 11/403,756, 6 pp.
Office Action dated Oct. 29, 2007, received in related case U.S. Appl. No. 11/695,944, 6 pp.
Office Action dated Oct. 9, 2008, received in related case U.S. Appl. No. 11/932,441, 4 pp.

Oleynikov et al., "In Vivo Camera Robots Provide Improved Vision for Laparoscopic Surgery," Computer Assisted Radiology and Surgery (CARS), Chicago, IL, Jun. 23-26, 2004b.
Oleynikov et al., "In Vivo Robotic Laparoscopy," Surgical Innovation, Jun. 2005, 12(2): 177-181.
Oleynikov et al., "Miniature Robots Can Assist in Laparoscopic Cholecystectomy," Journal of Surgical Endoscopy, 19-4: 473-476, 2005.
O'Neill, "Surgeon takes new route to gallbladder," The Oregonian, Jun. 2007, 2 pp.
Orlando et al., (2003), "Needle and Trocar Injuries in Diagnostic Laparoscopy under Local Anesthesia: What Is the True Incidence of These Complications?" Journal of Laparoendoscopic & Advanced Surgical Techniques 13(3): 181-184.
Park et al., "Trocar-less Instrumentation for Laparoscopy: Magnetic Positioning of Intra-abdominal Camera and Retractor," Ann Surg, Mar. 2007; 245(3): 379-384.
Park et al., "Experimental studies of transgastric gallbladder surgery: cholecystectomy and cholecystogastric anastomosis (videos)," Gastrointestinal Endoscopy, 2005; 61(4): 601-606.
Palm, William, "Rapid Prototyping Primer" May 1998 (revised Jul. 30, 2002) (http://www.me.psu.edu/lamancusa/rapidpro/primer/chapter2.htm).
Patronik et al., "Development of a Tethered Epicardial Crawler for Minimally Invasive Cardiac Therapies," IEEE, pp. 239-240.
Patronik et al., "Crawling on the Heart: A Mobile Robotic Device for Minimally Invasive Cardiac Interventions," MICCAI, 2004, pp. 9-16.
Patronik et al., "Preliminary evaluation of a mobile robotic device for navigation and intervention on the beating heart," Computer Aided Surgery, 10(4): 225-232, Jul. 2005.
Peirs et al., "A miniature manipulator for integration in a self-propelling endoscope," Sensors and Actuators A, 2001, 92: 343-349.
Peters, "Minimally Invasive Colectomy: Are the Potential Benefits Realized?" Dis Colon Rectum 1993; 36: 751-756.
Phee et al., "Analysis and Development of Locomotion Devices for the Gastrointestinal Tract," IEEE Transaction on Biomedical Engineering, vol. 49, No. 6, Jun. 2002, pp. 613-616.
Phee et al., "Development of Microrobotic Devices for Locomotion in the Human Gastrointestinal Tract," International Conference on Computational Intelligence, Robotics and Autonomous Systems (CIRAS 2001), Nov. 28-30, (2001), Singapore.
Platt et al., "In Vivo Robotic Cameras can Enhance Imaging Capability During Laparoscopic Surgery," in the Proceedings of the Society of American Gastrointestinal Endoscopic Surgeons (SAGES) Scientific Conference, Ft. Lauderdale, FL, Apr. 13-16, 2005, I pg.
Preliminary Amendment filed Apr. 11, 2007, in related case U.S. Appl. No. 11/403,756, 7 pp.
Preliminary Amendment filed Jul. 30, 2008, in related case U.S. Appl. No. 12/171,413, 4 pp.
RCE and Amendment filed Jun. 13, 2007, in related case U.S. Appl. No. 11/403,756, 8 pp.
Rentschler et al., "Mobile In Vivo Biopsy and Camera Robot," Studies in Health and Infonnatics Medicine Meets Reality, vol. 119., pp. 449-454, IOS Press, Long Beach, CA, 2006e.
Rentschler et al., Mobile in Vivo Biopsy Robot, IEEE International Conference on Robotics and Automation, Orlando, Florida, May 2006, pp. 4155-4160.
Rentschler et al., "Miniature in vivo Robots for Remote and Harsh Environments," IEEE Transactions on Information Technology in Biomedicine, Jan. 2006; 12(1): 66-75.
Rentschler et al., "An In Vivo Mobile Robot for Surgical Vision and Task Assistance," Journal of Medical Devices, Mar. 2007, vol. 1: 23-29.
Rentschler et al., "In vivo Mobile Surgical Robotic Task Assistance," 1 pg.
Rentschler et al., "In vivo Robotics during the NEEMO 9 Mission," Medicine Meets Virtual Reality, Feb. 2007, I pg.
Rentschler et al.., "In Vivo Robots for Laparoscopic Surgery," Studies in Health Technology and Infonnatics—Medicine Meets Virtual Reality, ISO Press, Newport Beach, CA, 2004a, 98: 316-322.

(56) References Cited

OTHER PUBLICATIONS

Rentschler et al., "Mechanical Design of Robotic In Vivo Wheeled Mobility," ASME Journal of Mechanical Design, 2006a, pp. I-II.
Rentschler et al., "Mobile In Vivo Camera Robots Provide Sole Visual Feedback for Abdominal Exploration and Cholecystectomy," Journal of Surgical Endoscopy, 20-I: 135-138, 2006b.
Rentschler et al., "Mobile In Vivo Robots Can Assist in Abdominal Exploration," from the Proceedings of the Society of American Gastrointestinal Endoscopic Surgeons (SAGES) Scientific Conference, Ft. Lauderdale, FL, Apr. 13-16, 2005b.
Rentschler et al., "Modeling, Analysis, and Experimental Study of In Vivo Wheeled Robotic Mobility," IEEE Transactions on Robotics, 22 (2): 308-321, 2005c.
Rentschler et al., "Natural Orifice Surgery with an Endoluminal Mobile Robot," The Society of American Gastrointestinal Endoscopic Surgeons, Dallas, TX, Apr. 2006d, 14 pp.
Rentschler et al., "Theoretical and Experimental Analysis of In Vivo Wheeled Mobility," ASME Design Engineering Technical Conferences: 28th Biennial Mechanisms and Robotics Conference, Salt Lake City, Utah, Sep. 28-Oct. 2, 2004, pp. 1-9.
Rentschler et al., "Toward In Vivo Mobility," Studies in Health Technology and Informatics—Medicine Meets Virtual Reality, ISO Press, Long Beach, CA, 2005a, III: 397-403.
Response to Rule 312 Amendment in related case U.S. Appl. No. 11/695,944, dated Jan. 12, 2009, 2 pp.
Riviere et al., "Toward Active Tremor Canceling in Handheld Microsurgical Instruments," IEEE Transactions on Robotics and Automation, Oct. 2003, 19(5): 793-800.
Rosen et al., "Force Controlled and Teleoperated Endoscopic, Grasper for Minimally Invasive Surgery-Experimental Performance Evaluation," IEEE Transactions of Biomedical Engineering, Oct. 1999; 46(10): 1212-1221.
Rosen et al., "Objective Laparoscopic Skills Assessments of Surgical Residents Using Hidden Markov Models Based on Haptic Information and Tool/Tissue Interactions," Studies in Health Technology and Infonnatics—Medicine Meets Virtual Reality, Jan. 2001, 7 pp.
Rosen et al., "Spherical Mechanism Analysis of a Surgical Robot for Minimally Invasive Surgery—Analytical and Experimental Approaches," Studies in Health Technology and Infonnatics—Medicine Meets Virtual Reality, pp. 442-448, Jan. 2005.
Rosen et al., "Task Decomposition of Laparoscopic Surgery for Objective Evaluation of Surgical Residents' Learning Curve Using Hidden Markov Model," Computer Aided Surgery, vol. 7, pp. 49-61, 2002.
Rosen et al., "The Blue Dragon—A System of Measuring the Kinematics and the Dynamics of Minimally Invasive Surgical Tools In-Vivo," Proc. of the 2002 IEEE International Conference on Robotics and Automation, Washington, DC, pp. 1876-1881, May 2002.
Ruurda et al., "Robot-Assisted surgical systems: a new era in laparoscopic surgery," Ann R. Coll Surg Engl., 2002; 84: 223-226.
Ruurda et al., "Feasibility of Robot-Assisted Laparoscopic Surgery," Surgical Laparoscopy, Endoscopy & Percutaneous Techniques, 2002; 12(1):41-45.
Sackier et al., "Robotically assisted laparoscopic surgery," Surgical Endoscopy, 1994; 8: 63-66.
Salky, "What is the Penetration of Endoscopic Techniques into Surgical Practice?" Digestive Surgery, 2000; 17:422-426.
Satava, "Surgical Robotics: The Early Chronicles," Surgical Laparoscopy, Endoscopy & Percutaneous Techniques, 2002; 12(1): 6-16.
Schippers et al., (1996) "Requirements and Possibilities of Computer-Assisted Endoscopic Surgery," In: Computer Integrated Surgery: Technology and Clinical Applications, pp. 561-565.
Schurr et al., "Robotics and Telemanipulation Technologies for Endoscopic Surgery," Surgical Endoscopy, 2000; 14: 375-381.
Schwartz, "In the Lab: Robots that Slink and Squirm," The New York Times, Mar. 27, 2007, 4 pp.
Sharp LL-151-3D, http://www.sharp3d.com, 2006, 2 pp.
Slatkin et al., "The Development of a Robotic Endoscope," Proceedings of the 1995 IEEE International Conference on Robotics and Automation, pp. 162-171, 1995.
Smart Pill "Fastastic Voyage: Smart Pill to Expand Testing," http://www.smartpilldiagnostics.com, Apr. 13, 2005, 1 pg.
Southern Surgeons Club (1991), "A prospective analysis of 1518 laparoscopic cholecystectomies," N. Eng. 1 Med. 324 (16): 1073-1078.
Stefanini et al., "Modeling and Experiments on a Legged Microrobot Locomoting in a Tubular Compliant and Slippery Environment," Int. Journal of Robotics Research, vol. 25, No. 5-6, pp. 551-560, May-Jun. 2006.
Stiff et al.., "Long-term Pain: Less Common After Laparoscopic than Open Cholecystectomy," British Journal of Surgery, 1994; 81: 1368-1370.
Strong, et al., "Efficacy of Novel Robotic Camera vs. a Standard Laproscopic Camera," Surgical Innovation vol. 12, No. 4, Dec. 2005, Westminster Publications, Inc., pp. 315-318.
Suzumori et al., "Development of Flexible Microactuator and its Applications to Robotics Mechanisms," Proceedings of the IEEE International Conference on Robotics and Automation, 1991: 1622-1627.
Taylor et al., "A Telerobotic Assistant for Laparoscopic Surgery," IEEE Eng Med Biol, 1995; 279-287.
Tendick et al.. (1993), "Sensing and Manipulation Problems in Endoscopic Surgery: Experiment, Analysis, and Dbservation," Presence 2( 1): 66-81.
Abbott et al., "Design of an Endoluminal NOTES Robotic System," from the Proceedings of the 2007 IEEE/RSJ Int'l Conf. on Intelligent Robot Systems, San Diego, CA, Oct. 29-Nov. 2, 2007, pp. 410-416.
Allendorf et al., "Postoperative Immune Function Varies Inversely with the Degree of Surgical Trauma in a Murine Model," Surgical Endoscopy 1997; 11:427-430.
Ang, "Active Tremor Compensation in Handheld Instrument for Microsurgery," Doctoral Dissertation, tech report CMU-RI-TR-04-28, Robotics Institute, Carnegie Mellon Unviersity, May 2004, 167pp.
Applicant Amendment after Notice of Allowance under Rule 312, filed Aug. 25, 2008, in related case U.S. Appl. No. 11/695,944, 6pp.
Applicant Response to Office Action dated Apr. 17, 2007, in related case U.S. Appl. No. 11/552,379, filed Aug. 8, 2007, 7 pp.
Applicant Response to Office Action dated Aug. 18, 2006, in related case U.S. Appl. No. 11/398,174, filed Nov. 7, 2006, 8pp.
Applicant Response to Office Action dated Aug. 21, 2006, in related case U.S. Appl. No. 11/403,756, filed Nov. 21, 2006, 52pp.
Applicant Response to Office Action dated Oct. 29, 2007, in related case U.S. Appl. No. 11/695,944, filed Jan. 22, 2008, 6pp.
Atmel 8005X2 Core, http://www.atmel.com, 2006, 186pp.
Bailey et al., "Complications of Laparoscopic Surgery," Quality Medical Publishers, Inc., 1995, 25pp.
Ballantyne, "Robotic Surgery, Telerobotic Surgery, Telepresence, and Telementoring," Surgical Endoscopy, 2002; 16: 1389-1402.
Bauer et al., "Case Report: Remote Percutaneous Renal Percutaneous Renal Access Using a New Automated Telesurgical Robotic System," Telemedicine Journal and e-Health 2001; (4): 341-347.
Begos et al., "Laparoscopic Cholecystectomy: From Gimmick to Gold Standard," J Clin Gastroenterol, 1994; 19(4): 325-330.
Berg et al., "Surgery with Cooperative Robots," Medicine Meets Virtual Reality, Feb. 2007, 1 pg.
Breda et al., "Future developments and perspectives in laparoscopy," Eur. Urology 2001; 40(1): 84-91.
Breedveld et al., "Design of Steerable Endoscopes to Improve the Visual Perception of Depth During Laparoscopic Surgery," ASME, Jan. 2004; vol. 126, pp. 1-5.
Breedveld et al., "Locomotion through the Intestine by means of Rolling Stents," Proceedings of the ASME Design Engineering Technical Conferences, 2004, pp. 1-7.
Calafiore et al., Multiple Arterial Conduits Without Cardiopulmonary Bypass: Early Angiographic Results,: Ann Thorac Surg, 1999; 67: 450-456.
Camarillo et al., "Robotic Technology in Surgery: Past, Present and Future," The American Journal of Surgery, 2004; 188: 2S-15.

(56) References Cited

OTHER PUBLICATIONS

Cavusoglu et al., "Telesurgery and Surgical Simulation: Haptic Interfaces to Real and Virtual Surgical Environments," In McLaughliin, M.L., Hespanha, J.P., and Sukhatme, G., editors. Touch in virtual environments, IMSC Series in Multimedia 2001, 28pp.
Cavusoglu et al., "Robotics for Telesurgery: Second Generation Berkeley/UCSF Laparoscopic Telesurgical Workstation and Looking Towards the Future Applications," Industrial Robot: An International Journal, 2003; 30(1): 22-29.
Chanthasopeephan et al., (2003), "Measuring Forces in Liver Cutting: New Equipment and Experimenal Results," Annals of Biomedical Engineering 31: 1372-1382.
Choi et al., "Flexure-based Manipulator for Active Handheld Microsurgical Instrument," Proceedings of the 27th Annual International Conference of the IEEE Engineering in Medicine and Biology Society (EMBS), Sep. 2005, 4pp.
Cuschieri, "Technology for Minimal Access Surgery," BMJ, 1999, 319: 1-6.
Dakin et al., "Comparison of laparoscopic skills performance between standard instruments and two surgical robotic systems," Surg Endosc., 2003; 17: 574-579.
Dumpert et al., "Improving in Vivo Robot Visioin Quality," from the Proceedings of Medicine Meets Virtual Realtiy, Long Beach, CA, Jan. 26-29, 2005. 1 pg.
Dumpert et al., "Stereoscopic In Vivo Surgical Robots," IEEE Sensors Special Issue on In Vivo Sensors for Medicine, Jan. 2007, 10 pp.
Examiner Interview Summary dated Aug. 6 and Aug. 12, 2008, in related case U.S. Appl. No. 11/695,944, 1 pg.
Examiner Interview Summary dated May 9, 2008, in related case U.S. Appl. No. 11/695,944, 1 pg.
Examiner Interview Summary dated Nov. 30, 2006, in related case U.S. Appl. No. 11/398,174, 2pp.
Falcone et al., "Robotic Surgery," Clin. Obstet. Gynecol. 2003, 46(1): 37-43.
Faraz et al., "Engineering Approaches to Mechanical and Robotic Design for Minimaly Invasive Surgery (MIS)," Kluwer Academic Publishers (Boston), 2000, 13pp.
Fearing et al., "Wing Transmission for a Micromechanical Flying Insect," Proceedings of the 2000 IEEE International Conference to Robotics & Automation, Apr. 2000; 1509-1516.
Fireman et al., "Diagnosing small bowel Crohn's desease with wireless capsule endoscopy," Gut 2003; 52: 390-392.
Flynn et al., "Tomorrow's Surgery: micromotors and microbots for minimally invasive procedures," Minimally Invasive Surgery & Allied Technologies.
Franklin et al., "Prospective Comparison of Open vs. Laparoscopic Colon Surgery for Carcinoma: Five-Year Results," Dis Colon Rectum, 1996; 39: S35-S46.
Fraulob et al., "Miniature assistance module for robot-assisted heart surgery," Biomed. Tech. 2002, 47 Suppl. 1, Pt. 1: 12-15.
Fukuda et al., "Mechanism and Swimming Experiment of Micro Mobile Robot in Water," Proceedings of the 1994 IEEE International Conference on Robotics and Automation, 1994: 814-819.
Fukuda et al., "Micro Active Catheter System with Multi Degrees of Freedom," Proceedings of the IEEE International Conference on Robotics and Automation, May, 1994, pp. 2290-2295.
Fuller et al., "Laparoscopic Trocar Injuries: A Report from a U.S. Food and Drug Administration (FDA) Center for Devices and Radiological Health (CDRH) Systematic Technology Assessment of Medical Products (STAMP) Committe," U.S. Food and Drug Adminstration, available at http://www.fdaJ:?;ov, Finalized: Nov. 7, 2003; Updated: Jun. 24, 2005, 11 pp.
Grady, "Doctors Try New Surgery for Gallbladder Removal," The New York Times, Apr. 20, 2007, 3 pp.

Tendick et al., "Applications of Micromechatronics in Minimally Invasive Surgery," IEEE/ASME Transactions on Mechatronics, 1998; 3(1): 34-42.
Thomann et al., "The Design of a new type of Micro Robot for the Intestinal Inspection," Proceedings of the 2002 IEEE Intl. Conference on Intelligent Robots and Systems, Oct. 2002: 1385-1390.
U.S. Appl. No. 60/180,960, filed Feb. 2000.
U.S. Appl. No. 60/956,032, filed Aug. 15, 2007.
U.S. Appl. No. 60/983,445, filed Oct. 29, 2007.
U.S. Appl. No. 60/990,062, filed Nov. 26, 2007.
U.S. Appl. No. 60/990,076, filed Nov. 26, 2007.
U.S. Appl. No. 60/990,086, filed Nov. 26, 2007.
U.S. Appl. No. 60/990,106, filed Nov. 26, 2007.
U.S. Appl. No. 60/990,470, filed Nov. 27, 2007.
U.S. Appl. No. 61/025,346, filed Feb. 1, 2008.
U.S. Appl. No. 61/030,588, filed Feb. 22, 2008.
U.S. Appl. No. 61/030,617, filed Feb. 22, 2008.
Way et al., (editors), "Fundamentals of Laparoscopic Surgery," Churchill Livingstone Inc., 1995, 14 pp.
Wolfe et al., "Endoscopic Cholecystectomy: An analysis of Complications," Arch. Surg. Oct. 1991; 126: 1192-1196.
Worn et al., "Espirit Project No. 33915: Miniaturised Robot for Micro Manipulation (MINIMAN)", Nov. 1998; http://www.ipr.ira.ujka.de/-microbot/miniman.
Yu et al., "Microrobotic Cell Injection," Proceedings of the 2001 IEEE International Conference on Robotics and Automation, May 2001; 620-625.
Yu, BSN, RN, "M2ATM Capsule Endoscopy a Breakthrough Diagnostic Tool for Small Intestine Imagining, " vol. 25, No. 1, Gastroenterology Nursing, pp. 24-27.
International Search Report and Written Opinion of international application No. PCT/US2010/061137, dated Feb. 11, 2011, 10 pp.
Abbou et al., "Laparoscopic Radical Prostatectomy with a Remote Controlled Robot," The Journal of Urology, Jun. 2001, 165: 1964-1966.
Glukhovsky et al.., "The development and application of wireless capsule endoscopy," Int. J. Med. Robot. Comput. Assist. Surgery, 2004; I (1): 114-123.
Gong et al., Wireless endoscopy, Gastrointestinal Endoscopy 2000; 51(6): 725-729.
Hanly et al., "Value of the SAGES Learning Center in introducing new technology," Surgical Endoscopy, 2004; 19 (4):477-483.
Hanly et al., "Robotic Abdominal Surgery," The American Journal of Surgery 188 (Suppl.to Oct. 1994): 19S-26S, 2004.
Heikkinen et al., "Comparison of laparoscopic and open Nissen fundoplication two years after operation: A prospective randomized trial," Surgical Endoscopy, 2000; 14: 1019-1023.
Hissink, "Olympus Medical develops capsule camera technology," Dec. 2004, accessed Aug. 29, 2007, http://www.letsgodigital.org , 3 pp.
Horgan et al., "Technical Report: Robots in Laparoscopic Surgery," Journal of Laparoendoscopic & Advanced Surgical Techniques, 2001; 11(6): 415-419.
Stoianovici et al., "Robotic Tools for Minimally Invasive Urologic Surgery", Jan. 1, 2002, pp. 1-17.
Cleary et al., "State of the Art in Surgical Rootics: Clinical Applications and Technology Challenges", "Computer Aided Surgery", Jan. 1, 2002, pp. 312-328, vol. 6.
Green, "Telepresence Surgery", Jan. 1, 1995, Publisher: IEEE Engineering in Medicine and Biology.
Franzino, "The Laprotek Surgical System and the Next Generation of Robotics," Surg Clin North Am, 2003 83(6): 1317-1320.
Guber et al., "Miniaturized Instrument Systems for Minimally Invasive Diagnosis and Therapy," Biomedizinische Technic. 2002, Band 47, Erganmngsband 1: 198-201.

\* cited by examiner

MEDICAL INFLATION, ATTACHMENT AND DELIVERY DEVICES AND RELATED METHODS

CROSS-REFERENCE TO RELATED APPLICATIONS

This is a continuation-in-part of U.S. application Ser. No. 12/192,663, filed Aug. 15, 2008 and entitled "Medical Inflation, Attachment, and Delivery Devices and Related Methods," which claims priority to Provisional Application No. 60/956,032, filed Aug. 15, 2007; Provisional Application No. 60/990,062, filed Nov. 26, 2007; and Provisional Application No. 60/990,470, filed Nov. 27, 2007; all of which are hereby incorporated herein by reference in their entireties.

GOVERNMENT SUPPORT

This invention was made with government support under Grant No. WS1XWH-08-02-0043 awarded by the U.S. Army Medical Research and Materiel Command within the Department of Defense. Accordingly, the government has certain rights in this invention.

TECHNICAL FIELD

The embodiments disclosed herein relate to various medical devices and related components, including robotic and/or in vivo medical devices and related components, along with related procedures and methods. Certain embodiments include various cavity inflation or structural retention system embodiments, including inflatable devices, scaffold-like devices, and externally-supported wall retention devices. Further embodiments include various medical device attachment and control components, including attachment pin devices and magnetic attachment devices. Additional embodiments include various medical device delivery devices that can be used to deliver various types of medical devices, including in vivo devices, to target medical treatment areas, including tubular devices with operational distal ends that provide for simple delivery, control, and retrieval of various medical devices.

BACKGROUND

Invasive surgical procedures are essential for addressing various medical conditions. When possible, minimally invasive procedures such as laparoscopy are preferred.

However, known minimally invasive technologies such as laparoscopy are limited in scope and complexity due in part to 1) mobility restrictions resulting from using rigid tools inserted through access ports, and 2) limited visual feedback. Known robotic systems such as the da Vinci® Surgical System (available from Intuitive Surgical, Inc., located in Sunnyvale, Calif.) are also restricted by the access ports, as well as having the additional disadvantages of being very large, very expensive, unavailable in most hospitals, and having limited sensory and mobility capabilities.

There is a need in the art for improved surgical methods, systems, and devices.

SUMMARY

One embodiment disclosed herein relates to a body cavity spatial support device having an inflatable body and an inflation mechanism. In one embodiment, the body has a generally cylindrical shape, while in another embodiment it has a generally donut shape. Alternatively, the device can have two or more inflatable bodies.

Another embodiment disclosed herein relates to a collapsible body cavity spatial support device. The device has at least three links hingedly coupled to each other and is configured to have a collapsed configuration and a deployed configuration.

A further embodiment disclosed herein relates to a pin having a needle tip and a retention component. The pin can be configured to be inserted through a cavity wall and be urged away from the cavity to maintain a procedural space in the cavity. According to one implementation, two or more pins are used cooperatively to maintain the procedural space.

Yet another embodiment disclosed herein relates to a pin having a grasping component configured to attach to an outer portion of the cavity wall. In one embodiment, two or more of these pins can be used cooperatively to maintain the procedural space.

One further embodiment disclosed herein relates to a procedural space maintenance system having at least two modular components that are coupled to each other and configured to be positioned inside a cavity of a patient. In one embodiment, the components each have at least one magnet. The system further comprises at least one external magnet configured to urge the at least two modular components away from the cavity and thereby maintain a procedural space in the cavity. In an alternative embodiment, the at least two modular components each have a mating or coupling component configured to couple with a medical device.

Another embodiment disclosed herein relates to a device positioning system having at least two modular components that are coupled to each other and configured to be positioned inside a cavity of a patient and attached to an interior cavity wall. The components are configured to couple together to create an attachment component along which a medical device can be positioned. Alternatively, the modular components have at least two legs to allow the system to be positioned in the cavity (instead of the attachment components for attaching to the interior wall).

A further embodiment disclosed herein relates to a device positioning and control system having at least one pin that is inserted through the cavity wall and coupled to an arm of a medical device positioned inside the body cavity. The pin can be used to maintain the position of the device and, according to a further embodiment, assist with the operation of the arm.

Yet another embodiment disclosed herein relates to a delivery or removal device having a tubular body, a device lumen, a wire lumen, and a wire disposed through the device and wire lumens. In accordance with one embodiment, the wire has an attachment component. In another embodiment, the tubular body has a protrusion at a distal end of the body. In a further embodiment, the protrusion is a deployable protrusion. In yet another embodiment, the protrusion has a device receiving component.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

DETAILED DESCRIPTION

Figure 1A:
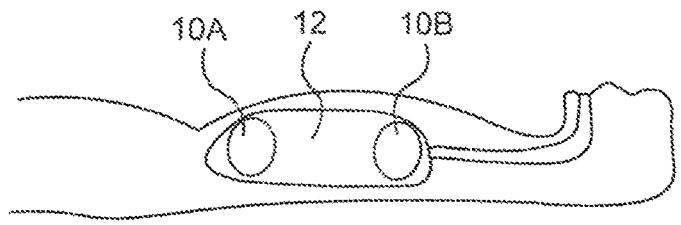
FIG. 1A is a side cutaway view depicting an inflatable device for maintaining procedural space in a body cavity, according to one embodiment.

The various systems and devices disclosed herein relate to devices for use in medical procedures and systems. More specifically, the various embodiments relate to various cavity inflation or structural retention system embodiments, various medical device attachment and control components, and various medical device delivery, control, and retrieval devices, all of which can be used in various procedural devices and systems.

It is understood that the various embodiments of cavity structural retention systems, device attachment components, and device delivery, control, and retrieval systems and other types of devices disclosed herein can be incorporated into or used with any known medical devices, including, but not limited to, robotic or in vivo devices as defined herein.

For example, the various embodiments disclosed herein can be incorporated into or used with any of the medical devices disclosed in copending U.S. application Ser. No. 11/932,441 (filed on Oct. 31, 2007 and entitled "Robot for Surgical Applications"), Ser. No. 11/695,944 (filed on Apr. 3, 2007 and entitled "Robot for Surgical Applications"), Ser. No. 11/947,097 (filed on Nov. 27, 2007 and entitled "Robotic Devices with Agent Delivery Components and Related Methods), Ser. No. 11/932,516 (filed on Oct. 31, 2007 and entitled "Robot for Surgical Applications"), Ser. No. 11/766,683 (filed on Jun. 21, 2007 and entitled "Magnetically Coupleable Robotic Devices and Related Methods"), Ser. No. 11/766,720 (filed on Jun. 21, 2007 and entitled "Magnetically Coupleable Surgical Robotic Devices and Related Methods"), Ser. No. 11/966,741 (filed on Dec. 28, 2007 and entitled "Methods, Systems, and Devices for Surgical Visualization and Device Manipulation"), Ser. No. 12/171,413 (filed on Jul. 11, 2008 and entitled "Methods and Systems of Actuation in Robotic Devices"), 60/956,032 (filed Aug. 15, 2007), 60/990,062 (filed on Nov. 26, 2007), 60/990,076 (filed Nov. 26, 2007), 60/990,086 (filed on Nov. 26, 2007), 60/990,106 (filed on Nov. 26, 2007), 60/990,470 (filed on Nov. 27, 2007), 61/030,588 (filed on Feb. 22, 2008), and 61/030,617 (filed on Feb. 22, 2008), all of which are hereby incorporated herein by reference in their entireties.

In an exemplary embodiment, any of the various embodiments disclosed herein can be incorporated into or used with a natural orifice translumenal endoscopic surgical device, such as a NOTES device. Those skilled in the art will appreciate and understand that various combinations of features are available including the features disclosed herein together with features known in the art.

Certain device implementations disclosed in the applications listed above can be positioned within a body cavity of a patient, including certain devices that can be positioned against or substantially adjacent to an interior cavity wall, and related systems. An "in vivo device" as used herein means any device that can be positioned, operated, or controlled at least in part by a user while being positioned within a body cavity of a patient, including any device that is positioned substantially against or adjacent to a wall of a body cavity of a patient, further including any such device that is internally actuated (having no external source of motive force), and additionally including any device that may be used laparoscopically or endoscopically during a surgical procedure. As used herein, the terms "robot," and "robotic device" shall refer to any device that can perform a task either automatically or in response to a command.

Certain implementations disclosed herein relate to cavity inflation or cavity structural retention devices or systems that are configured to provide space within the cavity of a patient for purposes of operating various medical devices and components within the cavity to perform one or more of various medical procedures, including, for example, the various medical devices and procedures disclosed in the various applications listed above and incorporated herein.

FIGS. 1A-1D, 2A-2C, and 3 depict various embodiments of inflatable devices that can be used to provide or create procedural space in a body cavity.

Figure 1B:
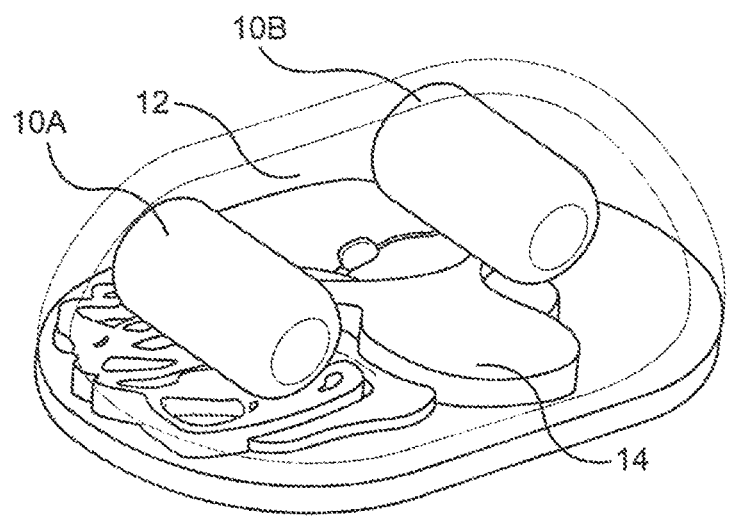
FIG. 1B is a perspective cutaway view of the device of FIG. 1A.
Figure 1C:
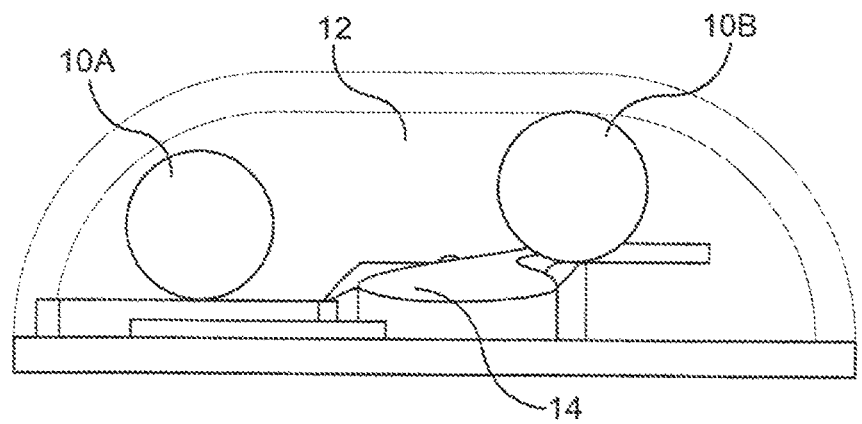
FIG. 1C depicts another side cutaway view of the device of FIG. 1A.
Figure 1D:
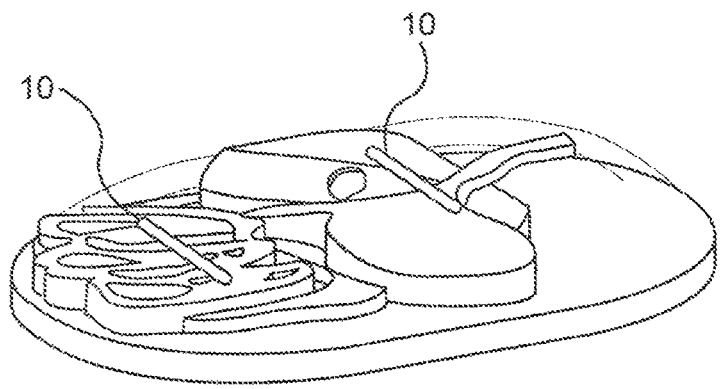
FIG. 1D shows a perspective cutaway view of the uninflated device of FIG. 1A.

FIGS. 1A-1D depict one example of an inflatable cavity inflation system 10A, 10B, according to one embodiment. In this embodiment, the system 10A, 10B has two inflatable components 10A, 10B, which can also be referred to herein as "balloons." The two balloons 10A, 10B can be inserted into and positioned in a body cavity as best shown in FIGS. 1A-1C such that they create or provide space within the cavity that allows a user (such as a doctor or surgeon) to operate various devices and/or perform various procedures within the space in the cavity. The two balloons 10A, 10B can be positioned in any fashion within the cavity to maintain the surgical space in the cavity. Alternatively, one inflation balloon or more than two inflation balloons can be positioned in the body cavity.

According to one embodiment, the body cavity is the abdominal cavity 12 as shown best in FIGS. 1A-1C. In such an embodiment, the balloons 10A, 10B are positioned on or adjacent to the various organs and tissues 14 in the cavity 12. Alternatively, the cavity can be any known body cavity.

In one implementation, the inflatable components 10A, 10B are made of polyethylene terephthalate ("PET"), which is manufactured by Advanced Polymers, Inc. of Salem, N.H. Alternatively, the components 10A, 10B can be made of nylon. In a further alternative, the components 10A, 10B are made of polyurethane. In yet another alternative, the components 10A, 10B can be made of any known expandable, durable, biocompatible material that can be used in medical devices.

The inflatable components 10A, 10B in one embodiment have tubing (not shown) or any other such connection attached to the components 10A, 10B that can couple the components to an external pump (not shown) that can be used to inflate the balloons 10A, 10B. Alternatively, the inflatable components 10A, 10B each have an inflation device (not shown) disposed somewhere within or on each balloon 10A, 10B that can be used to inflate each balloon 10A, 10B. According to one embodiment, the inflation device is a robotic device with a pressurized cavity that is opened for "self" inflation of the balloon.

Figure 2A:
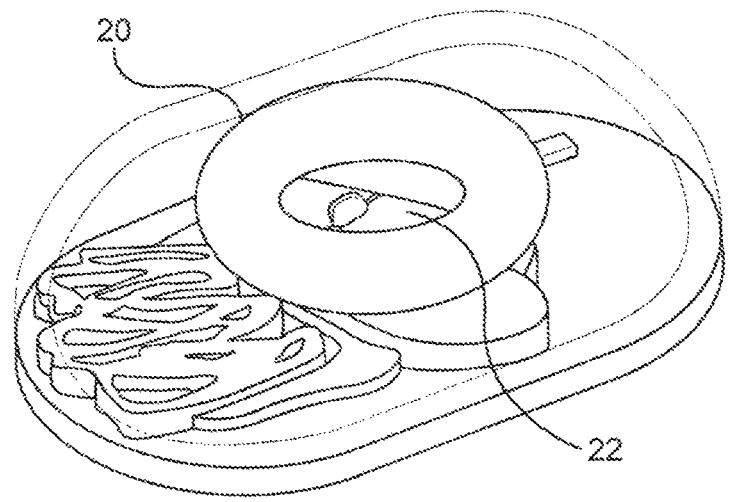
FIG. 2A is a perspective cutaway view of an inflatable device for maintaining procedural space in a body cavity, according to another embodiment.
Figure 2B:
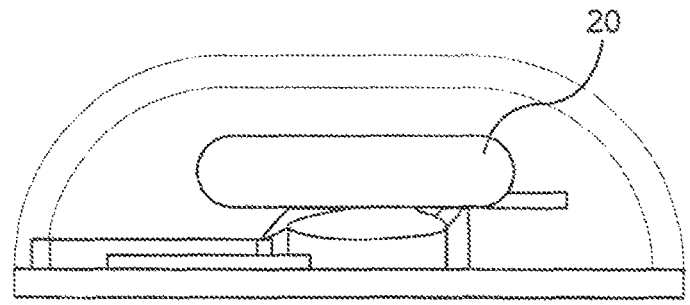
FIG. 2B is a side cutaway view of the device of FIG. 2A.
Figure 2C:
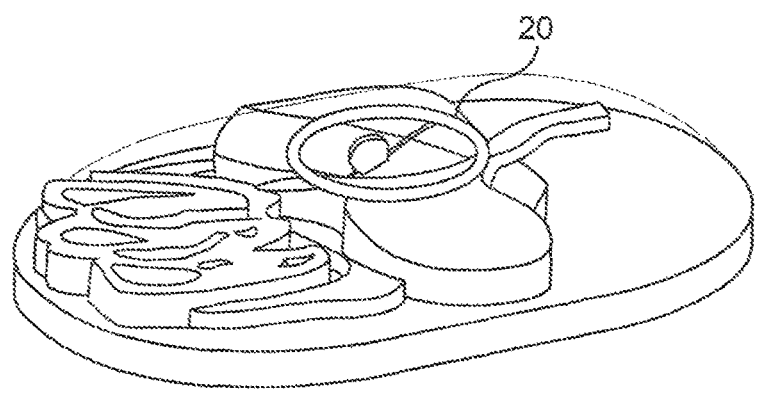
FIG. 2C is a side cutaway view of the uninflated device of FIG. 2A.

In an alternative embodiment as shown in FIGS. 2A-2C, a single inflatable component 20 is provided that is shaped like a donut or hoop. In this embodiment, the single component 20 can provide sufficient space within the patient's cavity to allow a user to operate a medical device and/or perform a medical procedure. According to one implementation, the donut-shaped balloon 20 can be positioned over the target procedural site such that the open portion in the center of the balloon 22 forms or maintains a procedural cavity space for purposes of the procedure.

It is understood that such a donut-shaped balloon 20 can be made of the same material as the balloons 10A, 10B discussed above.

In use, any of the balloons 10A, 10B, 20 can be utilized in the following manner. The un-inflated balloon(s) can be positioned inside the cavity as shown for example in FIGS. 1D and 2C. Once positioned, the balloon (or balloons) is inflated to provide or create procedural space within the cavity. At the conclusion of the procedure, the balloon(s) can be deflated or the pressurized gas can be sucked out by an external pump, and then the balloon(s) can be removed.

Figure 3:
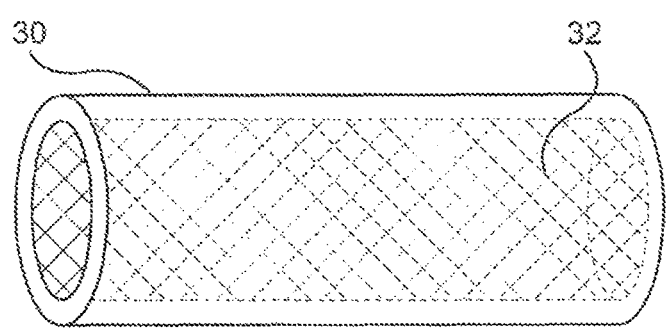
FIG. 3 is a schematic depiction of an inflatable balloon having an inner skeleton, according to one embodiment.

In a further alternative, any configuration of the balloons 10A, 10B, 20 can include internal structural members such as a series of pins or linkages inside of the balloons. FIG. 3 provides a schematic depiction of one embodiment of a balloon 30 having a skeleton or inner structure 32 disposed within the balloon 30. In the embodiment of FIG. 3, the skeleton 32 is a wire mesh similar to a stent. Alternatively, the skeleton 32 can be any structure configured to provide some deployable rigidity or structure to the balloon 30.

In use, the balloon 30 can be inserted in a deflated or undeployed state and, once positioned as desired, the inner structure 32 is triggered to expand into the deployed position as shown in FIG. 3 to provide or maintain a procedural space within a body cavity. According to one implementation, the inner skeleton 32 deploys in a fashion similar to a vascular stent, in which a tool of some kind is used to actuate the skeleton 32 to deploy. According to a further embodiment, the skeleton 32 locks into place upon deployment.

It is understood that many different medical devices, components, and procedures can be used in conjunction with the various inflatable device embodiments as shown in FIGS. 1A-1D, 2A-2C, and 3, including the positionable in vivo devices and various robotic devices and procedures described in the various applications disclosed and incorporated by reference above. That is, the various inflatable device embodiments can be used to provide and/or maintain procedural space in a body cavity such that any type procedure or related device for use in a body cavity can be used in the space, including the various devices and procedures disclosed and incorporated by reference above.

FIGS. 4A-4D depict a different support device 40 for providing or creating procedural space in a body cavity, according to one embodiment. This device 40 can be a scaffold-like structure intended to be expandable or deployable within the body cavity.

Figure 4A:
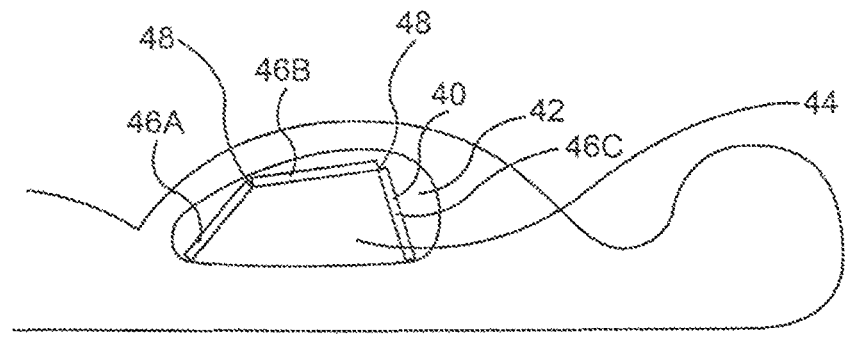
FIG. 4A is a side cutaway view depicting a device for maintaining procedural space in a body cavity, according to one embodiment.
Figure 4B:
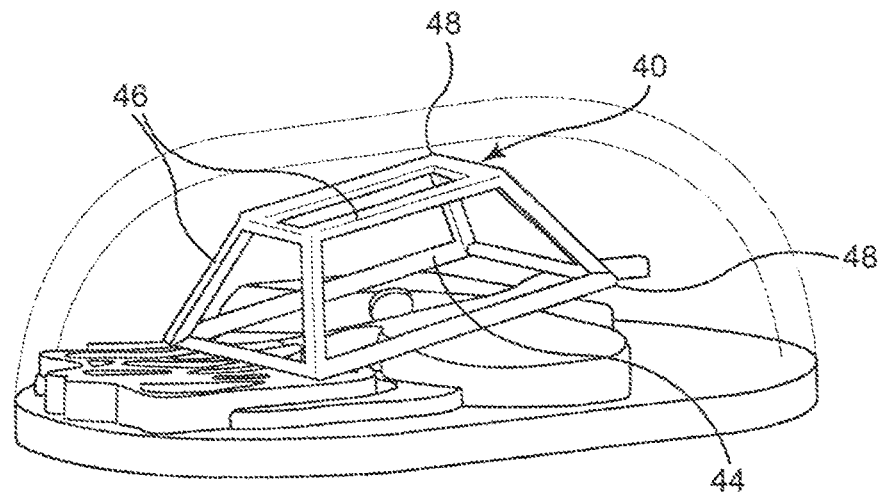
FIG. 4B is a perspective cutaway view of the device of FIG. 4A.
Figure 4C:
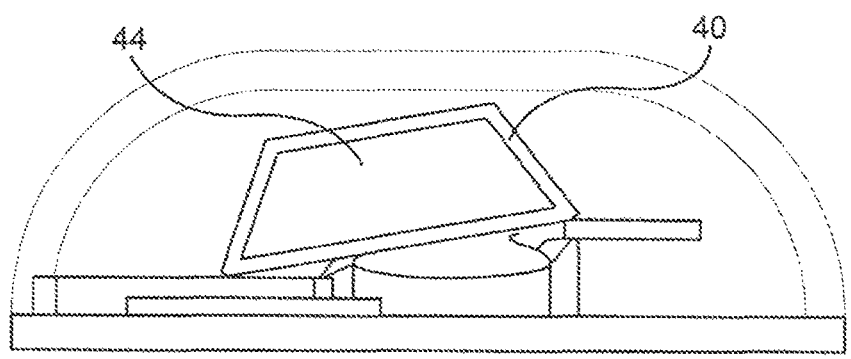
FIG. 4C is another side cutaway view of the device of FIG. 4A.
Figure 4D:
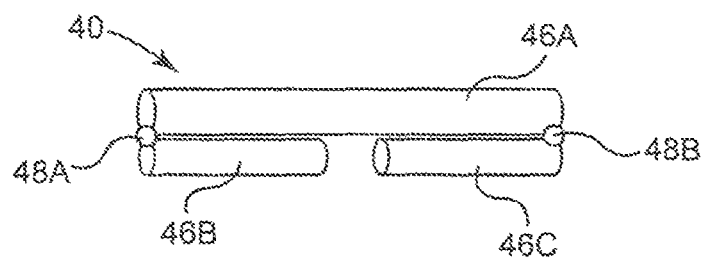
FIG. 4D is a schematic depiction of the device of FIG. 4A in a collapsed configuration.

As shown best in FIGS. 4A-4C, the support device 40 operates to hold the upper cavity wall up in a tent-like fashion. That is, the device 40 can be positioned within a body cavity such as an abdominal cavity 42 to provide a procedural space 44. The device 40 has a plurality of arms 46 (also referred to as "linkages") as shown in FIGS. 4A and 4B. In one embodiment, the arms 46 are all mechanically coupled to each other such that they can be converted between a collapsed configuration as depicted in FIG. 4D and the deployed configuration as shown in FIGS. 4A-4C. The device 40 is deployed by actuating the arms 46 into the configuration as shown. In one embodiment, the device 40 is deployed automatically through the use of springs or inflatable balloons that are attached at or otherwise positioned in the hinges 48 of the device 40. Alternatively, the device 40 has motors or hydraulics that can be used to mechanically deploy the device 40. In a further alternative, any known component that can urge the device 40 from the collapsed configuration to the deployed configuration can be coupled or otherwise associated with the hinges of the device 40.

The arms 46 of the device 40 can be made of any biocompatible polymers. Alternatively, the arms 46 can be made of stainless steel. In a further alternative, the arms 46 can be made of any known substantially rigid, biocompatible material.

It is understood that the arms 46 of the device 40 are coupled at joints 48, as best shown in FIGS. 4B and 4D, or other similar known connection components. It is further understood that these joints 48 can be any known pivot or hinge joints. Alternatively, the joints 48 can be universal joints with rotation in two planes.

In accordance with another implementation, externally-supported wall retention systems and devices are provided to create and/or maintain a procedural space in a body cavity.

It is understood that many different medical devices, components, and procedures can be used in conjunction with the various support device embodiments as shown in FIGS. 4A-4D, including the positionable in vivo devices and various robotic devices and procedures described in the various applications incorporated by reference above. That is, the various support device embodiments can be used to provide and/or maintain procedural space in a body cavity such that any type procedure or related device for use in a body cavity can be used in the space, including the various devices and procedures disclosed and incorporated by reference above.

FIGS. 5A-5D depict one embodiment of an externally-supported wall retention system. In this embodiment, the system relates to at least two retention pins similar to the pin 50 depicted in FIGS. 5A and 5B that can be inserted through the cavity wall, attached to the wall, and subsequently urged away from the cavity to create a procedural space within the cavity.

Figure 5A:
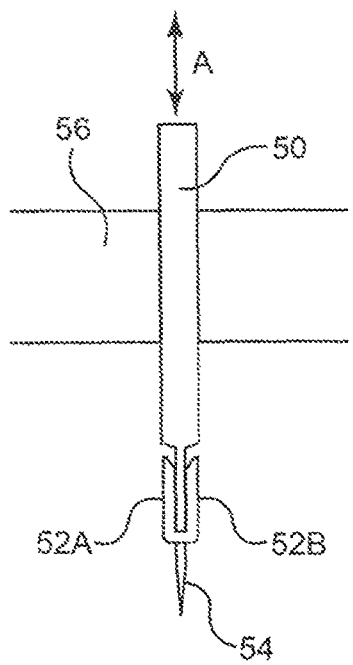
FIG. 5A is a side view of a wall retention pin having a retention component in the collapsed configuration, according to one embodiment.
Figure 5B:
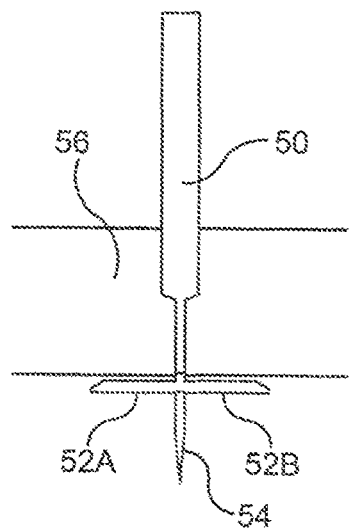
FIG. 5B is a side view the wall retention pin of FIG. 5A in which the retention component is in the deployed configuration.

As shown in FIGS. 5A and 5B, each pin 50 (also referred to herein as a "needle") has a distal end having a needle tip 54 and two leaves or toggle-like components 52A, 52B that are each pivotally attached to the pin 50 such that the leaves 52A, 52B can move between a collapsed position as shown in FIG. 5A and a deployed position as shown in FIG. 5B. In the collapsed position depicted in FIG. 5A, each of the leaves 52A, 52B are disposed in a position parallel to the length of the pin 50. In the deployed position depicted in FIG. 5B, each of the leaves 52A, 52B are disposed in a position perpendicular to the length of the pin 50.

In an alternative embodiment, any known toggle-like or attachment component can be provided near the distal end of the pin 50 to allow for insertion of the pin 50 through the cavity wall 56 and then capture of the interior portion of the wall while the pin 50 is being urged away from the cavity to create space within the cavity.

Figure 5C:
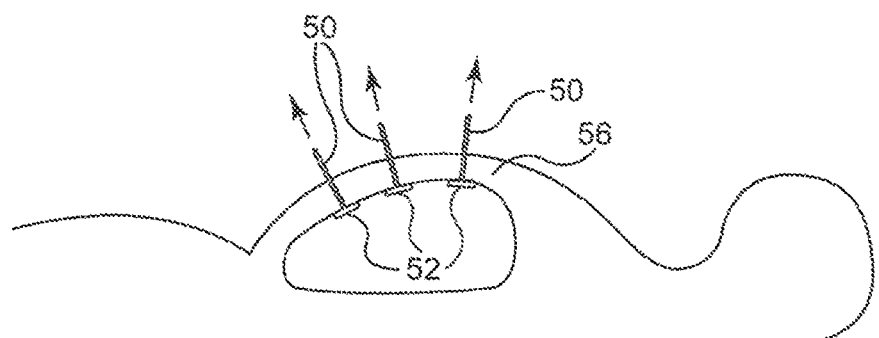
FIG. 5C is a side cutaway view of three wall retention pins similar to that of FIG. 5A in use, according to one embodiment.
Figure 5D:
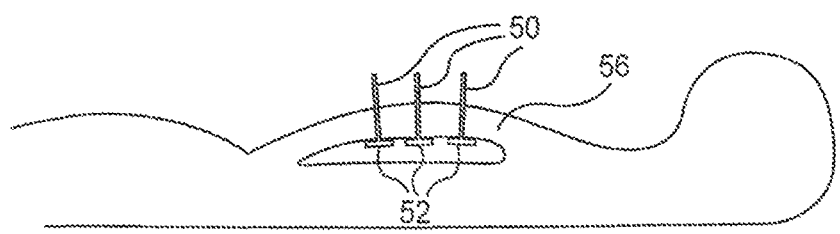
FIG. 5D is another side cutaway view of the three wall retention pins of FIG. 5C in a relaxed configuration in which the cavity wall is not being urged away from the cavity.

In use as best shown in FIGS. 5C and 5D, at least two pins or needles 50 are positioned in the cavity wall 56 such that the pins 50 are attached to the wall 56 and then can be urged away from the cavity 58 in the direction of the arrows in FIG. 5A to provide procedural space within the cavity 58. In one embodiment, each pin or needle 50 is inserted into the cavity wall 56 along the axis indicated by the letter A in FIG. 5C while the leaves 52A, 52B are in the collapsed position. Once the leaves 52A, 52B are inserted through the wall 56 and into the body cavity, the leaves 52A, 52B are moved into the deployed position as shown in FIG. 5B (and in FIGS. 5C and 5D). Each pin 50 can then be urged or moved in an outward direction (away from the patient) until the leaves 52A, 52B are in contact with the wall 56. According to one embodiment, sufficient force is applied to the pin 50 such that the leaves 52A, 52B can support the wall 56 and maintain an open cavity configuration, wherein the cavity wall 56 is urged away from the organs within the cavity, as shown in FIG. 5C.

In one embodiment, the force applied to the pin 50 or pins 50 is a manual force applied by the surgeon or assistant pulling on the pins with her or his hands. Alternatively, the force applied is a mechanical force provided by a device or by attaching the pins 50 to a stationary device.

Figure 6A:
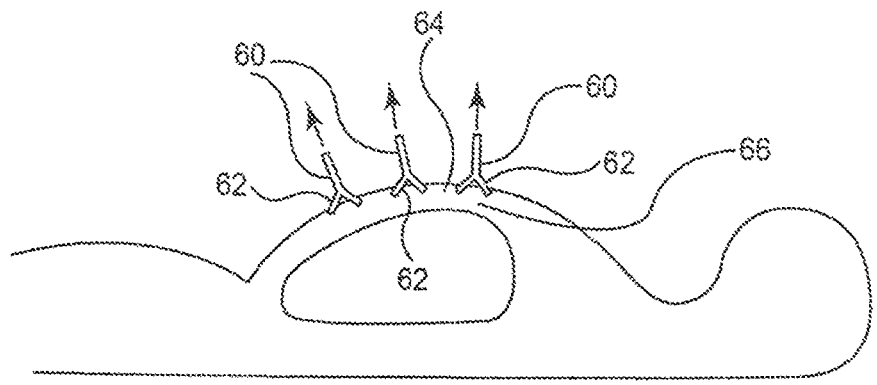
FIG. 6A is a side cutaway view of three wall retention pins, each having an attachment component, according to another embodiment.
Figure 6B:
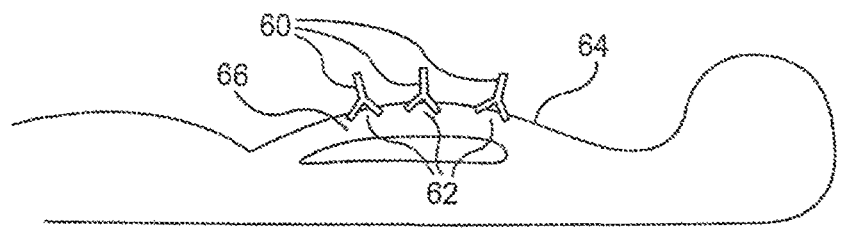
FIG. 6B is another side cutaway view of the three wall retention pins of FIG. 6A in a relaxed configuration in which the cavity wall is not being urged away from the cavity.

An alternative embodiment of an externally-supported wall retention system is provided in FIGS. 6A and 6B. In this embodiment, each of the pins 60 operate in a similar fashion as the pins 50 shown in FIGS. 5A-5D. That is, the pins 60 are attached to the cavity wall and urged to pull the wall away from the cavity to provide procedural space within the cavity. However, in contrast to the pins 50 described above, each pin 60 of FIGS. 6A and 6B is not inserted into the cavity and attached to the inner wall of the cavity. Instead, each pin 60 has an attachment component 62 that can be attached to an external portion of the patient outside the body cavity. That is, the attachment component 62 can attach to an external portion 64 of the cavity wall.

In one embodiment, the attachment component 62 is a "grasper" that attaches to the external portion 64 of the cavity wall 66 by grasping the external portion 64. Alternatively, the attachment component 62 has barbs or other components that can be inserted partially into the external portion 64 of the wall 66. In a further alternative, the attachment component 62 has an adhesive that is used to attach the component 62 to the wall 66. In use, once the attachment component 62 is attached to the wall 66 as shown in FIG. 6B, each pin 60 is urged away from the patient in the same fashion described above such that the pins 60 urge the wall 64 away from the body and thereby maintain an open cavity space as shown in FIG. 6A.

It is understood that many different medical devices, components, and procedures can be used in conjunction with the various externally-supported wall retention embodiments as shown in FIGS. 5A-5D and 6A-6B, including the positionable in vivo devices and various robotic devices and procedures described in the various applications incorporated by reference above. That is, the various wall retention device embodiments can be used to provide and/or maintain procedural space in a body cavity such that any type procedure or related device for use in a body cavity can be used in the space, including the various devices and procedures disclosed and incorporated by reference above.

FIGS. 7A-8B depict further exemplary implementations of externally-supported wall retention and device positioning systems and devices that create and/or maintain a procedural space in a body cavity while also providing for positioning one or more medical devices within the body cavity.

Figure 7A:
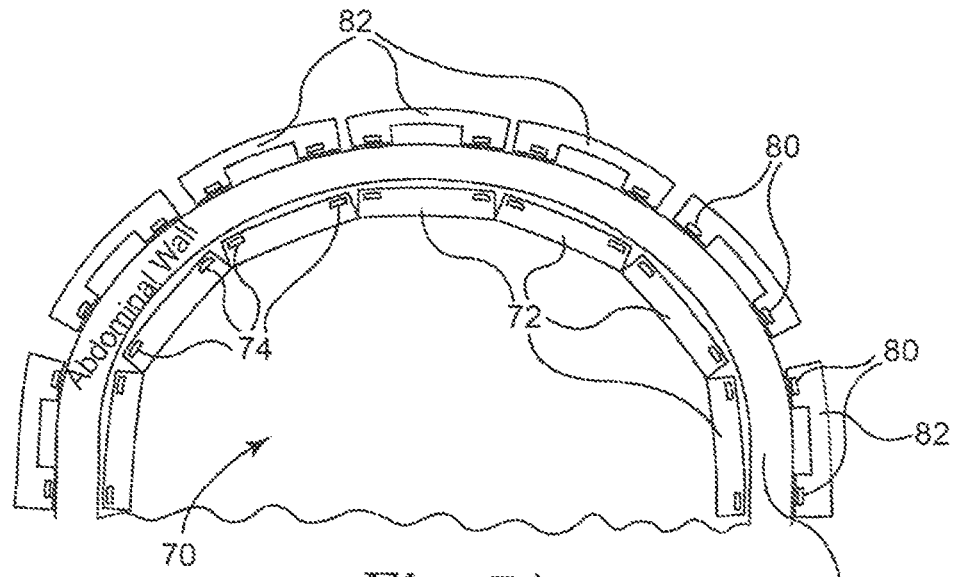
FIG. 7A is a side cutaway view of a wall retention system, according to one embodiment.
Figure 7B:
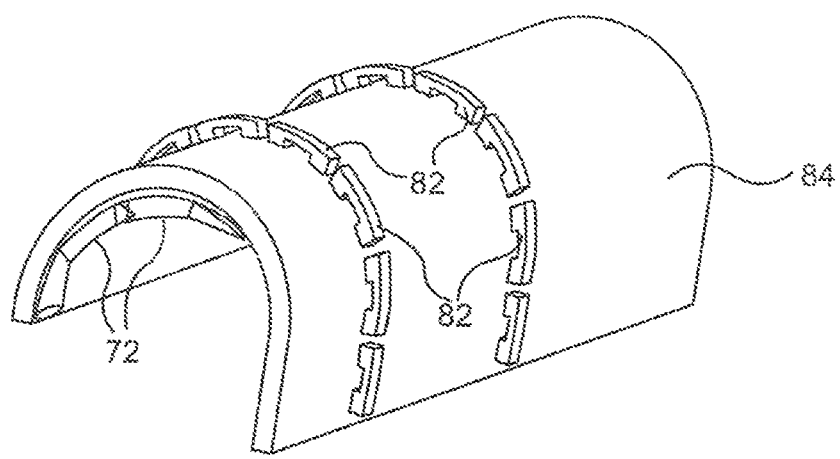
FIG. 7B is a perspective cutaway view of the wall retention system of FIG. 7A.
Figure 7C:
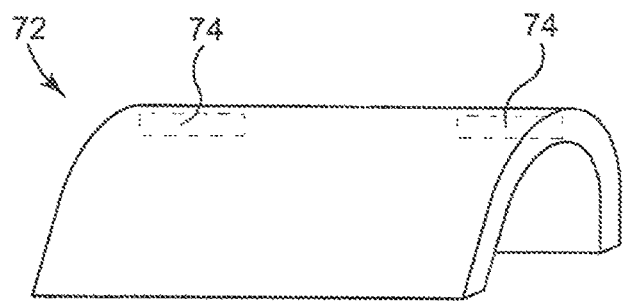
FIG. 7C is a perspective view of one modular component of a wall retention system, according to one embodiment.
Figure 7D:
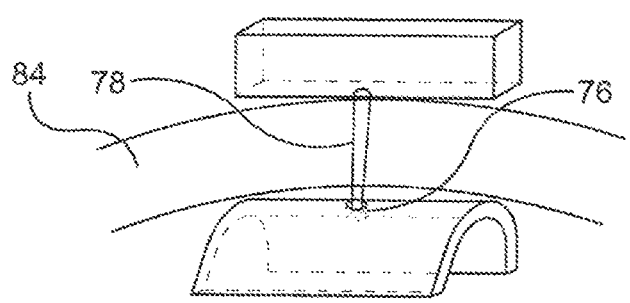
FIG. 7D is a perspective cutaway view of another modular component of a wall retention system, according to another embodiment.

FIGS. 7A-7D depict an embodiment of an externally-supported wall retention and device positioning system that provides for both maintaining the open configuration of the surgical cavity and for positioning a medical device within the cavity. In one implementation, the system as depicted provides for positioning one or more medical devices along an interior wall of the cavity. As shown in FIG. 7A, the device or system 70 has two or more modular components 72 (also referred to herein as "rail modules") that are hingedly coupled to each other. According to one embodiment, each of the modular components 72 has at least one magnet 74 disposed therein, as best shown in FIGS. 7A and 7C. Alternatively, each of the modular components 72 has at least one attachment point 76 to which a pin or needle 78 can attach, as best shown in FIG. 7D.

The device 70 as shown in FIG. 7A is configured such that each of the modular components 72 can be inserted through a small incision or a trocar-like tube into the surgical cavity. That is, the device 70 can be configured in an elongate shape such that its profile is small enough to be inserted through such an incision or tube.

After insertion, the modular components 72 of the device 70 are positioned against the interior of the cavity wall 84. In one embodiment, the device 70 is positioned against the wall 84 using exterior magnets 80 positioned outside the cavity as shown in FIGS. 7A and 7B. In one embodiment as shown, the magnets 80 are positioned in handles 82. This approach could provide a method for non-insufflating NOTES procedures if multiple devices 70 are positioned along the cavity wall 84. That is, it is possible to use this embodiment to create and/or maintain a procedural space in a body cavity without insufflation. The use of multiple modules 72 allows for the implementation of multiple magnets or needles for attachment to the cavity wall. This provides for a stronger attachment because the force applied by the multiple magnets to create a procedural space is greater than that created by one or two magnets.

Alternatively, the device 70 is positioned against the wall using exterior pins or needles 78, as shown in FIG. 7D.

Figure 8A:
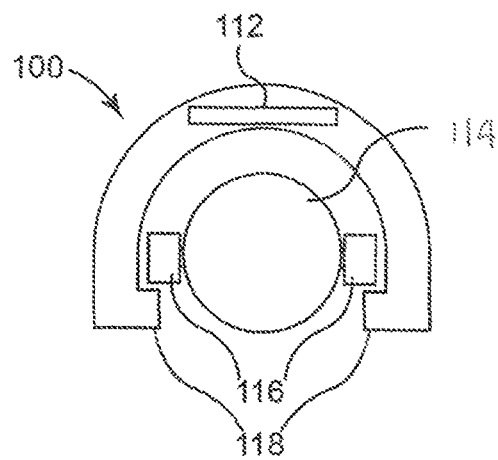
FIG. 8A is an end view of a modular component of a wall retention system, according to a further embodiment.
Figure 8B:
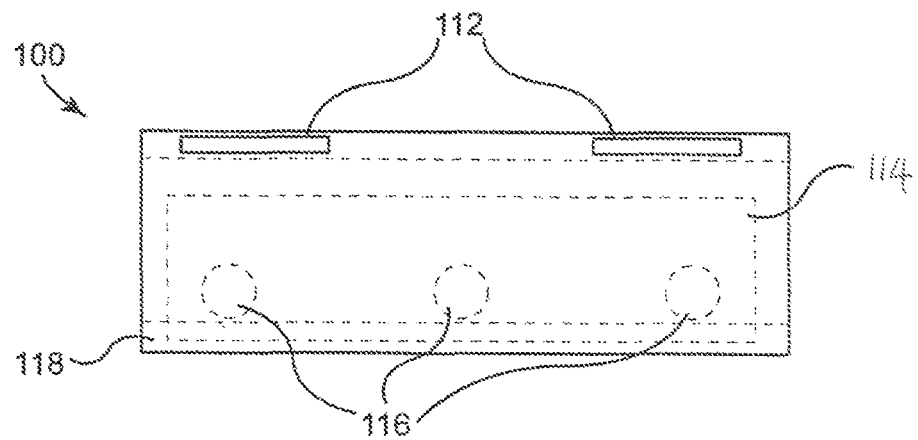
FIG. 8B is a side view of the modular component of FIG. 8A.

According to one alternative embodiment, a modular component 100 similar to those disclosed in FIGS. 7A-7D is shown in FIGS. 8A-8B that is configured to receive one or more medical devices along track or mating components in the modular components. Each module 100 in this embodiment has at least one attachment magnet 112 and one or more tracks or mating components 118 with which a robotic device 114 can moveably mate using a set of wheels or cogs 116 and along which the robotic device 114 can move. Thus, two or more modular components 100 can be connected to each other to create a "railway" that one or more medical devices can traverse to move around the procedural cavity (similar to the set of modules as shown in FIG. 7A).

Each module 100 as shown in FIG. 8A has at least one magnet 112 associated with or disposed within the module 100. Further, each module 100 has a mating component 118 associated with or defined by the module 100. A medical device 114 can be coupled with the rail module 100 by the mating component 116 on the device 114. In one embodiment as shown, the mating component 116 on the device 114 is a wheel or cog that can couple with the rail 118 on the module 100. In one embodiment, the device 114 can be maintained in a substantially fixed position such that the device 114 can move along the rail module 100 relative to the cavity. This module 100 can be positioned transversely or sagitally along the cavity wall. Alternatively, the module 100 can be positioned in any known fashion within the cavity to allow for transporting a medical device along a predetermined path. In a further embodiment, more than one module 100 is positioned within the cavity and coupled together (in a fashion similar to FIG. 7A) and the device 114 can be positioned within the coupled modules 100 so that the device 114 can traverse along the length of the coupled modules 100. Alternatively, more than one device can be placed along the coupled modules 100 or more than one set of coupled modules 100 can be positioned in the cavity.

One advantage of the multiple modules with multiple magnets is that the weight of the attached device can be distributed across multiple attachment points. Furthermore, if the device includes arms, this approach provides a more stabilized and distributed base for tissue manipulation forces.

It is understood that many different medical devices, components, and procedures can be used in conjunction with the various externally-supported wall retention and device positioning systems and device embodiments as shown in FIGS. 7A-8B, including the positionable in vivo devices and various robotic devices and procedures described in the various applications incorporated by reference above. That is, the various wall retention and device positioning embodiments can be used to provide and/or maintain procedural space in a body cavity while also providing for the positioning and/or attachment of one or more medical devices, such that any type of procedure or related device for use in a body cavity can be used and positioned in the space, including the various devices and procedures disclosed and incorporated by reference above.

FIGS. 9-12 depict exemplary implementations of device positioning systems and devices that provide for positioning one or more medical devices within the body cavity.

Figure 9:
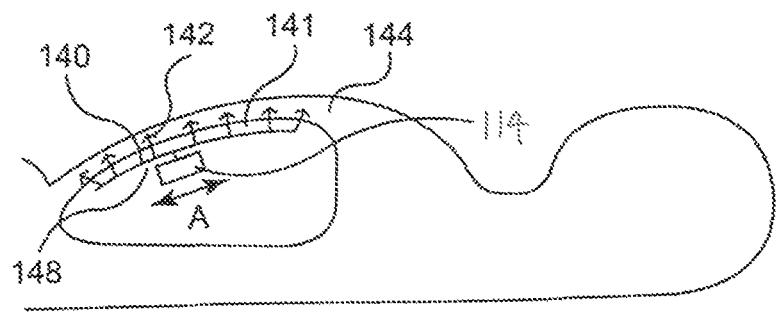
FIG. 9 is a side cutaway view of a device support system, according to one embodiment.

FIG. 9 depicts one embodiment of a modular "railed" device 140. In this embodiment, each module 141 has a hook or attachment component 142 that can attach to the cavity wall 144. In one embodiment as shown, each module 141 is attached to the wall 144 with a hook or similar attachment component 142 that penetrates the wall 144. Alternatively, each module 141 is attached to the wall using an adhesive. In a further alternative, each module 141 is attached to the wall by any known attachment method or device.

Each module 141 also has a track or mating component 148 that is capable of coupling with one or more medical devices. The coupling of each module 141 to each other or positioning of the modules 141 adjacent to each other creates a positioning device 140 along which a medical device 114 can move or be positioned.

Figure 10:
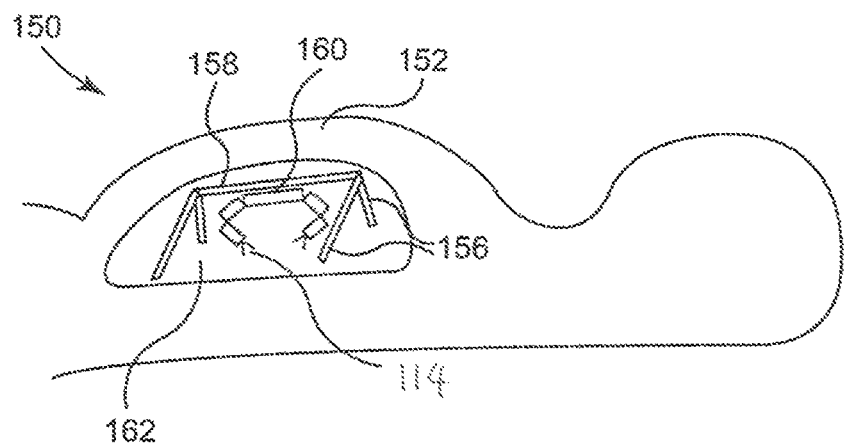
FIG. 10 is a side cutaway view of another device support system, according to another embodiment.

FIG. 10 depicts another embodiment of a positioning device 150. Instead of attaching with an attachment component to a cavity wall 152, this device 150 is supported in the cavity 162 using at least two legs or links 156 that are positioned along a bottom portion of the cavity to support the rail 158. In the embodiment depicted in FIG. 10, the device attachment component is a rail 158 along which the medical device 114 can move or be positioned. Alternatively, the device attachment component can be any such component along which the one or more medical devices 114 can be positioned. In the embodiment depicted in FIG. 10, the device 150 has four legs 156 that create a swing-set-like structure. A medical device 114 can be moveably attached to the rail 158 such that the medical device 114 can move back and forth along the rail 158.

In one alternative implementation, the railed device 150 can have robotic, or otherwise actuated, components. For example, the legs 156 can have actuators (not shown) that actuate the legs 156 to move such that the device 114 can be raised or lowered. In a further embodiment, the attachment point 160 where the medical device 114 is coupled to the rail 158 can be coupled to an actuator (not shown) such that the actuator can operate to move the device 114 along the rail 158.

In accordance with another implementation, the railed device 150 can support a medical device 114 as shown and described above while also providing cavity space maintenance. That is, the device 150 can also provide support to hold the upper cavity wall away from the lower cavity wall and therefore maintain the procedural cavity space.

Figure 11:
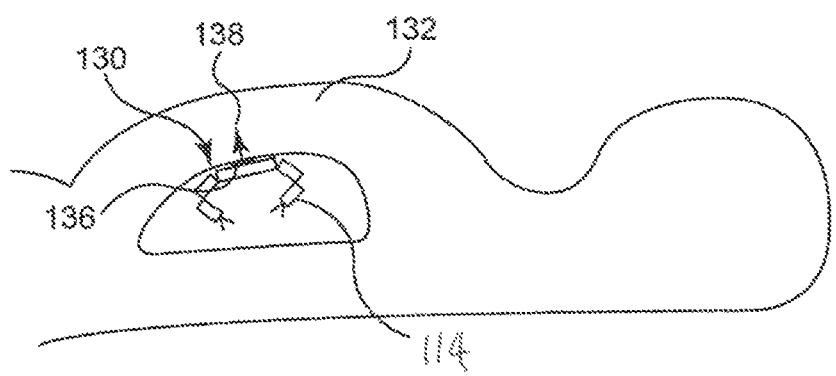
FIG. 11 is a side cutaway view of yet another device support system, according to a further embodiment.

FIG. 11 depicts another embodiment of a medical device positioning or attachment device 130. The device 130 has a wall attachment component 138 and a device attachment component 136. The wall attachment component 138 as shown in FIG. 11 is a hook that attaches to the cavity wall 132. Alternatively, the wall attachment component 138 can utilize an adhesive. In a further alternative, the wall attachment component 138 can be any known component for attaching to the cavity wall. Further, according to another implementation, attachment device 130 is made of a degradable material and thus need not be removed from the cavity wall after the procedure is completed.

The device attachment component 136 provides for removable attachment to a medical device 114. In one embodiment, the device attachment component 136 is a magnet that removably couples to the medical device 114. Alternatively, the attachment component 136 provides for a mechanical coupling with the medical device 114. In a further alternative, the attachment component 136 provides for any type of attachment method or device to attach to the medical device 114 such that the device 114 can be removed. In one implementation, the device 114 can be removed and a second device can be attached. In a further implementation, more than one medical device 114 can be attached.

Figure 12:
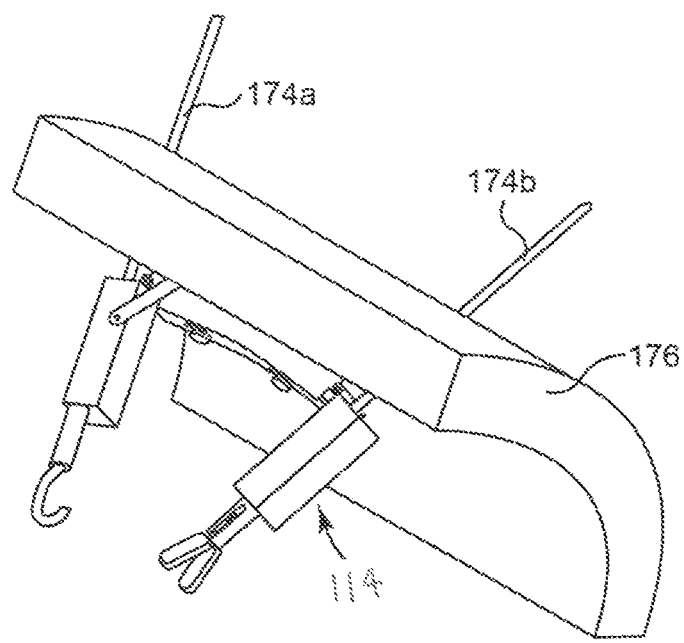
FIG. 12 is a perspective cutaway view of a device support and control system, according to another embodiment.

Another embodiment of a medical device attachment or positioning device is depicted in FIG. 12. In this embodiment, the medical device 114 is positioned against an interior cavity wall using two pins 174A, 174B inserted through the cavity wall and coupled to the device 114. In one embodiment, these pins 174A, 174B are thin needles that require no suturing or recovery time. According to one implementation, the pins 174 can be known needles currently used for amniocentesis and chorionic villi sampling. Alternatively, each pin 174A, 174B can be any pin-like or needle-like component capable of being inserted into the patient's body and coupled to the medical device 114 disposed within the patient's body. After insertion, the needles 174 are attached to the in vivo device 114. In one embodiment, only one pin is attached, thereby allowing the device 114 to rotate about the single attachment point. Alternatively, two pins are inserted to hold the robot in position, with additional needles inserted as needed to move the robot to a different orientation. In another implementation, these attachment pins can also be used in conjunction with magnets to position and/or attach the device.

The use of attachment pins provides a stable attachment of the medical device to or near the cavity wall. In those embodiments in which the medical device is controlled by some form of exterior component, the pins can assist in ensuring the medical device is positioned near or adjacent to the exterior handle or other exterior component. Alternatively, the pin length is controlled or manipulated to provide a vertical degree-of-freedom that would allow the medical device to move up and down relative to the pin and/or the body cavity. Attachment or coupling of the pins to the device includes self-assembly techniques that include magnets at the pin tips or semi-autonomous connection with the medical device. Alternatively, the pins are attached through surgeon assistance in vivo using endoscopic tools or other medical devices.

In one method, the pin or pins are inserted into the patient's body and then the medical device or devices are coupled to the pin(s). In another embodiment, the medical device is positioned against the cavity wall prior to insertion of the pin(s), and the pin (or pins) is inserted such that the pin couples to the device during insertion. Alternatively, the pin (or pins) is first inserted and then the medical device is coupled to the pin.

According to one embodiment, the pins 174 described herein can be used to assist with the attachment or positioning of one or more medical devices within a body cavity of an obese patient in which the cavity wall 176 has a thickness that makes it difficult or impossible to use magnetic attachment devices or methods.

It is understood that many different medical devices, components, and procedures can be used in conjunction with the various device positioning embodiments as shown in FIGS. 9-12, including the positionable in vivo devices and various robotic devices and procedures described in the various applications incorporated by reference above. That is, the various device positioning embodiments can be used to provide for the positioning and/or attachment of one or more medical devices, such that any type of procedure or related device for use in a body cavity can be used and positioned in the space, including the various devices and procedures disclosed and incorporated by reference above.

FIGS. 13-20B depict exemplary implementations of medical device 114 insertion and retraction devices.

Figure 13:
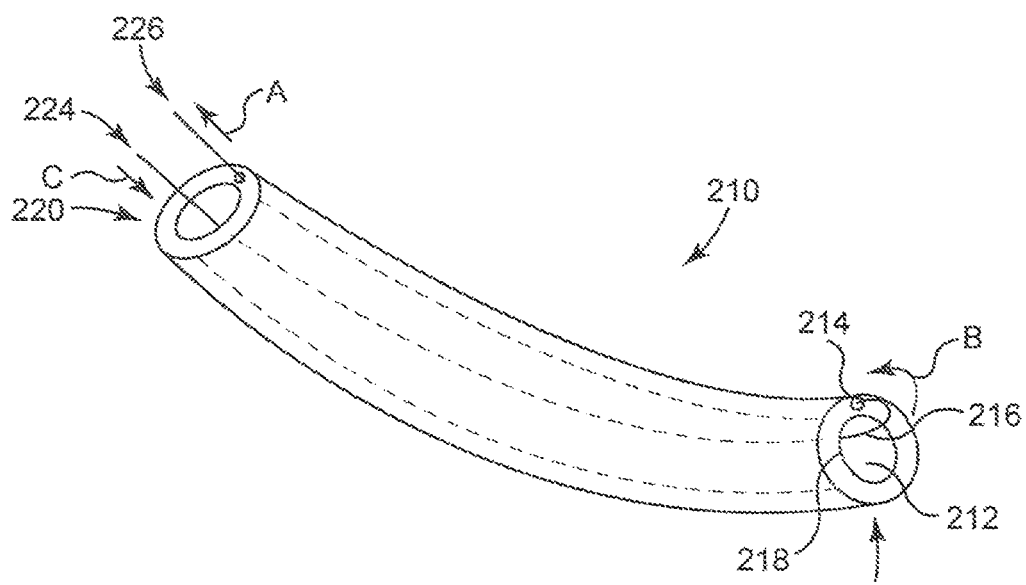
FIG. 13 is a perspective view of a procedural delivery device, according to one embodiment.

FIG. 13 depicts an overtube 210, according to one embodiment, for use in inserting a medical device into a patient's body and retracting the device (shown, for example, at 114 in FIGS. 14-16 and 18) from the body through the overtube 210. It is understood that the term "overtube" as used herein is intended to mean any medical procedural tube that is inserted into a patient and positioned such that further procedural devices can be inserted through the tube into the patient, retrieved through the tube from the patient, and/or such that the further procedural devices can be operated inside the patient through the tube. Thus, "overtube" includes any tube that is inserted down the patient's esophagus or through any incision or into any cavity and positioned such that other devices or instruments can be inserted into the patient's body.

The overtube 210 as shown in FIG. 13 defines a device lumen 212 through which a medical device, such as a robotic device, can be passed. In addition, the overtube 210 also defines a wire lumen 14 through which an insertion wire 216 can be passed. In the embodiment depicted in FIG. 13, the wire lumen 214 is defined in the outer wall 218 of the overtube 210 and has a diameter that is smaller than the device lumen 212.

In use, the overtube 210 allows a user to pull a medical device 114 through the overtube 210 from the proximal end 220 to the distal end 222 of the overtube 210. That is, according to one implementation, the insertion wire 216 is inserted through the device lumen 212 and also inserted through the wire lumen 214 as depicted in FIG. 13, such that the proximal end 224 of the wire 216 and the distal end 226 of the wire 216 both extend from the proximal end 220 of the overtube 210.

The proximal end 224 of the wire 216 is then attached to the device (not shown) to be pulled through the overtube 210. Alternatively, the wire 216 is attached to the device prior to positioning the wire 216 in the tube 210. The distal end 226 of the wire 216 is then pulled by the user such that the wire moves in the direction indicated by the arrows A, B, and C, thereby resulting in the device being pulled toward the distal end 222 of the overtube 210.

In one implementation, the wire 216 is a braided metal cable. Alternatively, the wire 216 is a nylon string. In yet another alternative, the wire can be any such wire, tether, thread, cord, or any other type of elongate flexible material that can be used in medical procedures such as the methods described herein.

According to one embodiment, the overtube 210 is a flexible polyethylene tube. Alternatively, the overtube can be any tube, cannula, or other type of hollow elongate object having a lumen that can be used for insertion of devices into, or use of devices within, a patient's body.

Figure 14:
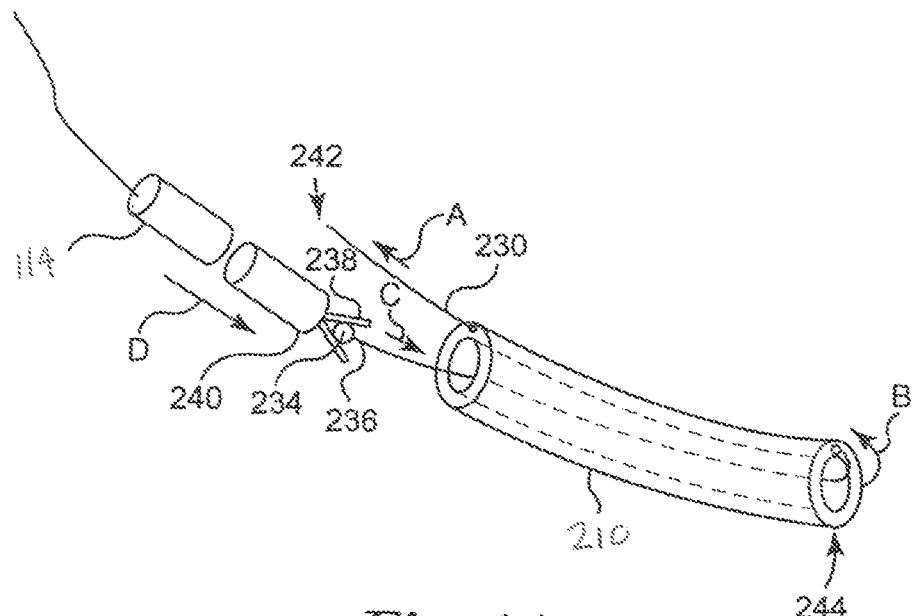
FIG. 14 is a perspective view of another delivery device, according to another embodiment.

FIG. 14 depicts one method and device for attachment of a wire 230 to a medical device 114 for device insertion. In this embodiment, the wire 230 has an attachment component 234 in the form of a ball coupled to the proximal end 236 of the wire 230. In use, the clamp 238 on the distal end 240 of the device 114 is clamped onto or otherwise coupled with the ball 234 on the wire 230. Upon attachment of the device 114 to the wire 230 via attachment of the clamp 238 to the ball 234, the user can pull the distal end 242 of the wire 230 to move the wire 230 as shown by the arrows A, B, and C to thereby pull the device 114 toward the distal end 244 of the overtube 210, which is the direction depicted by arrow D. Once the device 114 has reached the desired position, the user can operate the clamp 238 to release the ball 234 such that the device 114 can then be used to perform the intended procedure.

According to the embodiment depicted in FIG. 14 and discussed above, the attachment component 234 is a ball. Alternatively, the attachment component is a hook that can hook to a portion or component of the medical device. In another embodiment, the attachment component is a loop-shaped portion of string or cable that can be looped or otherwise coupled with an appropriate mating component on the medical device. Alternatively, the component 234 can be any shape or any component that allows for easy attachment to the medical device 114. In a further alternative, the attachment component 234 is a magnet that can magnetically couple with the device 114. In yet another alternative, the attachment component can be any component that can be used to removably attach the wire 230 to a medical device 114.

Figure 15:
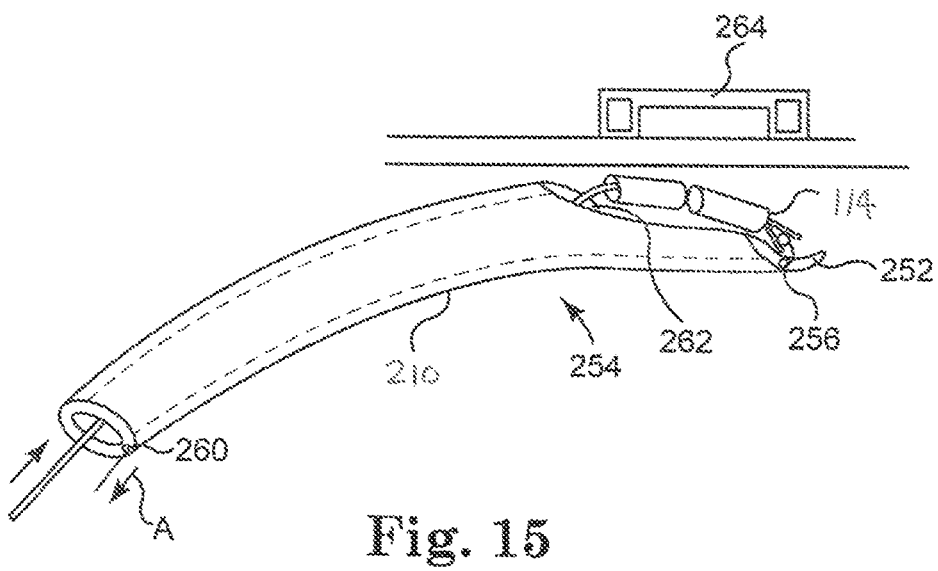
FIG. 15 is a side cutaway view of another delivery device, according to a further embodiment.

FIG. 15 depicts an alternative embodiment of an overtube 210 for insertion or delivery of a medical device. In this implementation, the overtube 210 has a protrusion 252 that protrudes or extends from the distal end 254 of the tube 210. The term "protrusion" shall encompass, for purposes of this application, any portion or component of the overtube 210, or a separate component, such as a lip or an extension, that protrudes or extends from the distal end 254 of the tube 210. According to one embodiment, the wire lumen 256 is defined in the protrusion 252 as shown in FIG. 15 and has a diameter that is smaller than the device lumen 262.

In use, the protrusion 252 as shown in FIG. 15 facilitates positioning of the medical device 114, which can be a robotic device according to one embodiment. That is, as the wire 260 is pulled as shown by arrow A, the wire 260 pulls the device 114 toward the protrusion 252 on the distal end 254 of the tube 210. Because the protrusion 252 extends beyond the distal end 254 of the tube, the device 114 exits from the device lumen 262 as it approaches the protrusion 252 and thus is pulled into or positioned in the target or procedural site in the patient's body. In an alternative step, a magnetic handle 264 or other magnetic component can be positioned externally to the body cavity and used to further position the device 114. Alternatively, any external positioning component can be utilized in conjunction with the overtube 210 to facilitate positioning the device as desired and/or with precision.

Figure 16:
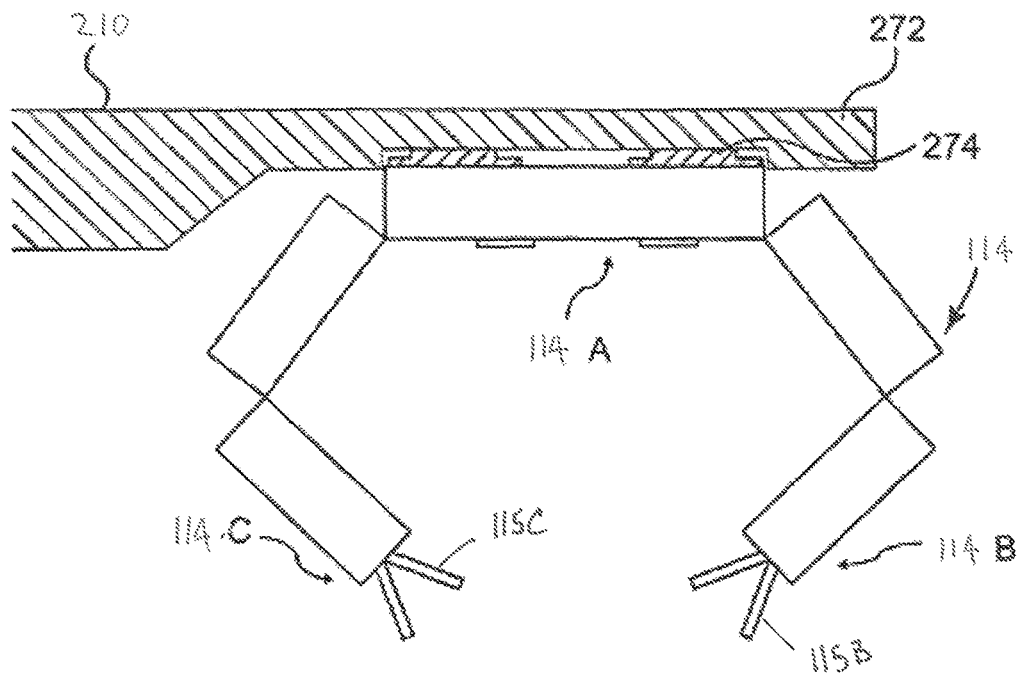
FIG. 16 is a side view of another delivery device component, according to another embodiment.

A further alternative implementation is depicted in FIG. 16, in which the overtube 210 has a protrusion 272 having an indentation or device receiving component (also referred to as a "docking component") 274 that is configured to receive a medical device 114 such that the device 114 can couple with or "dock" to the protrusion 272 or to the end of the overtube 210 for final positioning or even during the entire or a significant portion of the medical procedure. In this implementation, the coupling can be accomplished with magnets or mechanical attachment components such as claims or screws. In yet another embodiment, the medical device docks to the protrusion or to the overtube itself to charge onboard batteries, or to store a biopsy sample, or to exchange end-effectors. As shown, the device has a device body 114A with two arms 114B, 114C, each with an end-effector 115B, 115C.

Figure 17A:
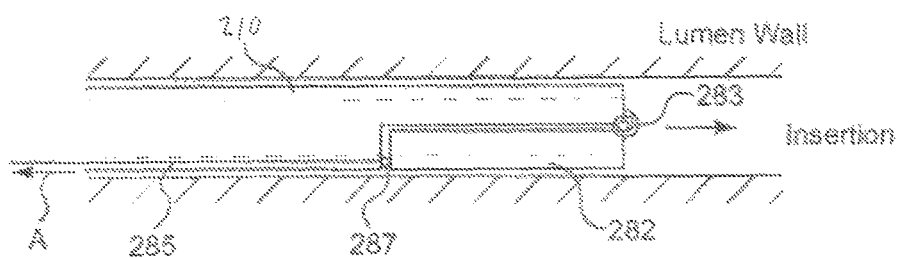
FIG. 17A is a side cutaway view of another delivery device, according to another embodiment.
Figure 17B:
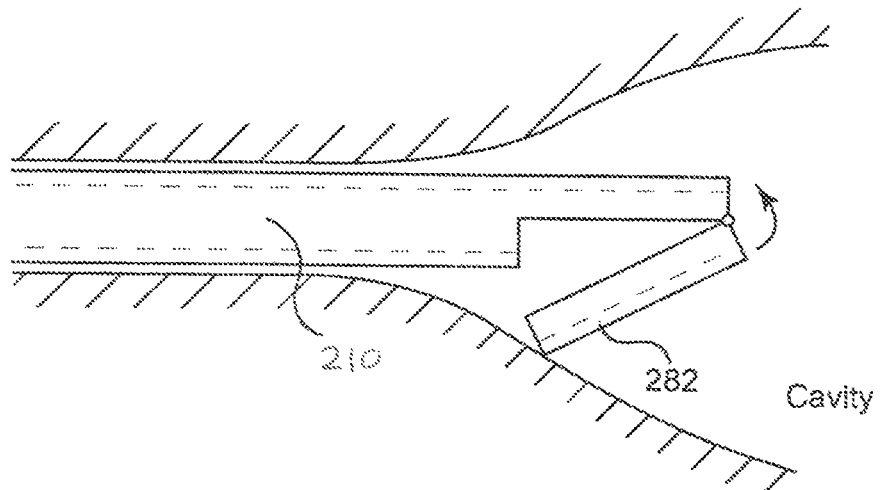
FIG. 17B is another side cutaway view of the delivery device of FIG. 17A.
Figure 17C:
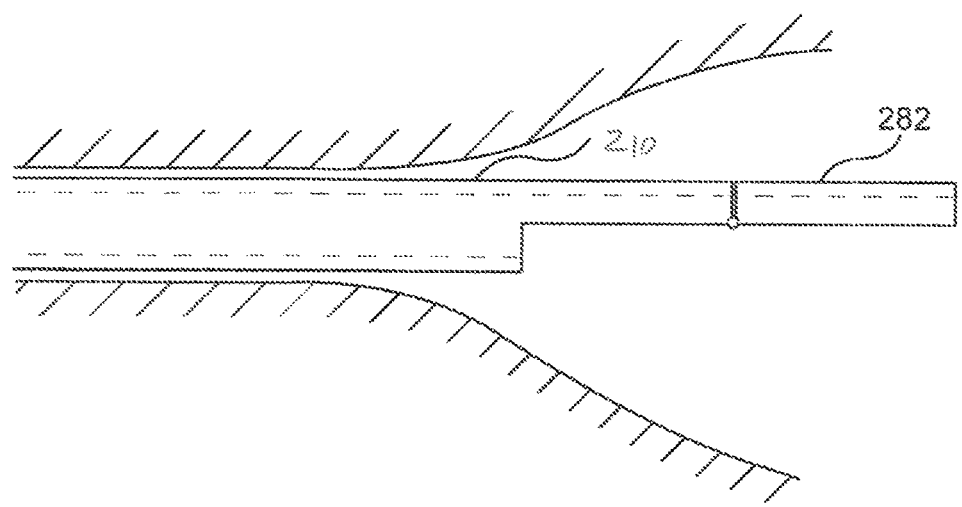
FIG. 17C is another side cutaway view of the delivery device of FIG. 17A.

Alternatively, the protrusion can be a deployable protrusion. For example, one embodiment of a deployable protrusion 282 is depicted in FIGS. 17A and 17B. In this embodiment, the protrusion 282 is movably coupled to the overtube 210 and can unfold using a spring 283, such as a torsional spring. FIG. 17A depicts the protrusion 282 in the undeployed position in which the torsional spring 283 is configured to urge the protrusion 282 into the deployed position but is retained in the undeployed or closed position by retention component 287. The retention component 287 can be a hook, latch, or any other actuable retention component that can be actuated to release the protrusion 282 from the undeployed position. FIG. 17B depicts the protrusion 282 at a position between the undeployed position and the deployed position and FIG. 17C depicts the protrusion 282 in the fully deployed position.

In use, the protrusion 282 can be maintained in the undeployed position during insertion. That is, according to one embodiment, the protrusion 282 is not be deployed until the overtube 210 is inserted into the patient. At this point, the protrusion 282 can then be deployed through a series of actuators or cables. For example, according to one embodiment as shown in FIG. 17A, the overtube 210 has a wire or cable 285 coupled to the retention component 287 such that the wire or cable 285 can be pulled in the direction of arrow A to actuate the retention component 287 to release the protrusion 282. Once released, the force applied to the protrusion 282 by the torsional spring 283 causes the protrusion 282 to move toward the deployed position as shown in FIG. 17B. FIG. 17C depicts the protrusion 282 after it has reached the deployed position.

Alternatively, the overtube 210 can have any other kind of overtube positioning component at its distal end. That is, any component that facilitates exit of the device from the device lumen and/or positioning of the device at the target area can be used with the overtube. For example, it is understood that the concept of this positioning component shall encompass any hole or gap defined in the tube that provides for positioning of the device in the same fashion that the protrusion accomplishes such positioning.

Figure 18:
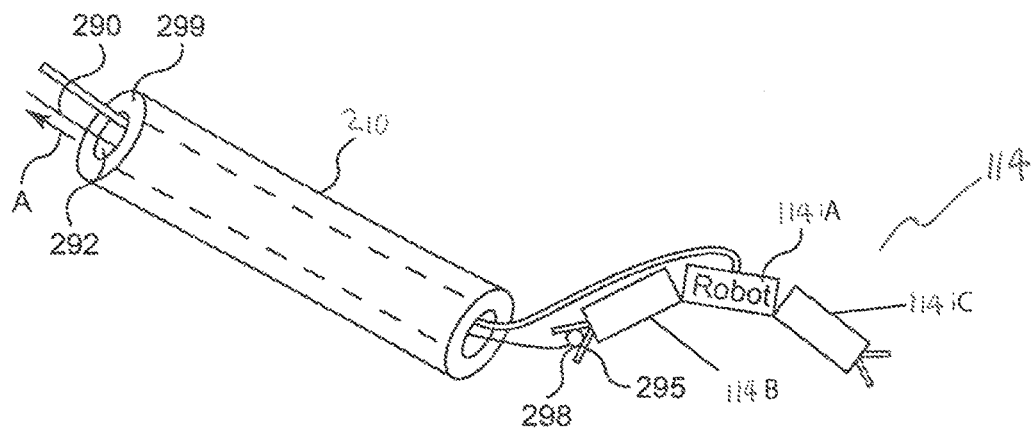
FIG. 18 is a perspective view of a retraction device, according to one embodiment.

In another embodiment, FIG. 18 depicts a method and device for retracting a device from an interior portion of a patient's body. More specifically, FIG. 18 depicts a retraction wire 290 that can be inserted through the device lumen 292 of the overtube 210 and into the procedural site. In use, the user can operate the clamp 295 or some other type of attachment component of the medical device 114 to attach to the wire attachment component 298, which in this embodiment is a ball. In the embodiment shown, the device 114 has a device body 114A with two arms 114B, 114C. Alternatively, the wire attachment component 298 can be any such attachment component as described above, including a magnet or any other component that provides for attachment of the wire 290 and the device 114. Once the device 114 is attached to the wire 290, the user pulls the wire 290 toward the proximal end 299 of the tube 294 (in the direction indicated by arrow A), thereby retracting the device 114 from the procedural site.

Figure 19A:
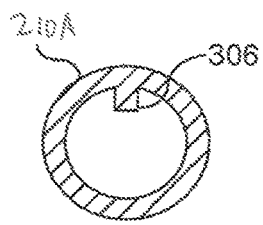
FIG. 19A is a cross-sectional depiction of an insertion device, according to one embodiment.
Figure 19B:
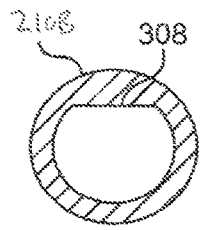
FIG. 19B is a cross-sectional depiction of another insertion device, according to one embodiment.
Figure 19C:
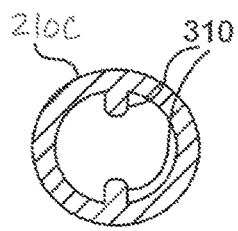
FIG. 19C is a cross-sectional depiction of a further insertion device, according to one embodiment.

FIGS. 19A, 19B, and 19C depict profiles of three different overtubes 210A, 210B, and 210C, according to three different embodiments. Each overtube has an orientation component 306, 308, and 310 that cooperates with the device to be inserted through the overtube 210A, 210B, or 210C to orient the device. More specifically, according to the embodiments depicted in FIGS. 19A, 19B, and 19C, the orientation component in each figure is configured to mate or couple with the body of the device being inserted through the overtube 210A, 210B, or 210C such that the device is forced to be oriented in a particular fashion as it passes through the overtube 210A, 210B, 210C, thereby facilitating the proper orientation of the device during insertion and/or positioning.

It is understood that FIGS. 19A, 19B, and 19C are merely exemplary, and that any orientation component configuration can be provided so long as it results in mating with the device to be inserted such that the device can be provided with the proper orientation.

Figure 20A:
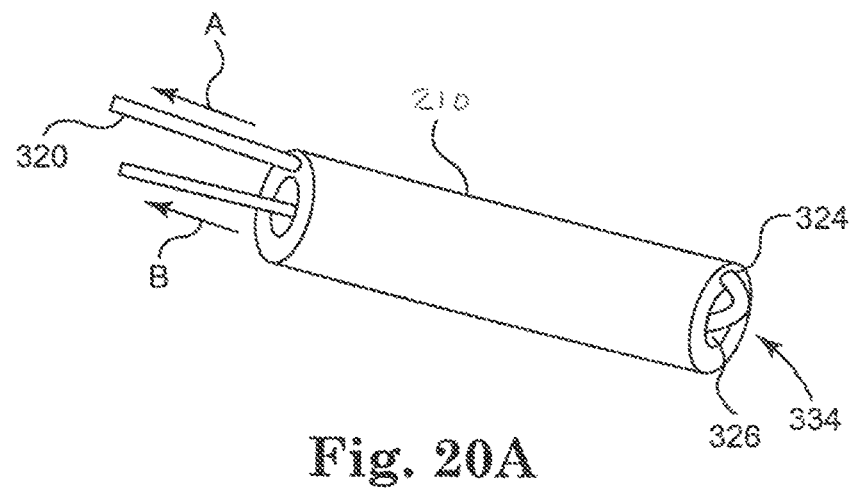
FIG. 20A is a perspective view of an insertion and retraction device, according to one embodiment.
Figure 20B:
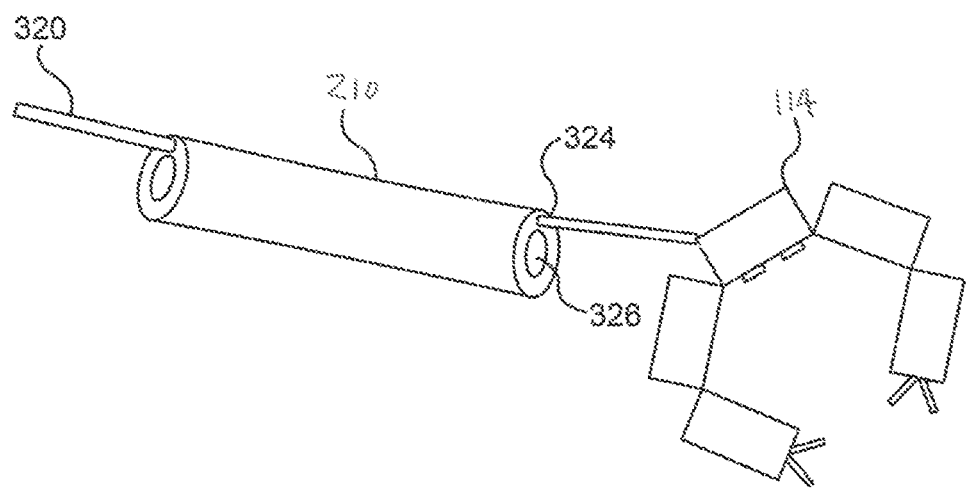
FIG. 20B is another perspective view of the device of FIG. 20A.

FIGS. 20A and 20B depict another method and device for inserting and retracting a medical device, according to one embodiment. In this embodiment, the connection component 320 (also referred to as a "tether") connecting the medical device 114 to the external controller (not shown) is disposed through the wire lumen 324 and the device lumen 326 of the overtube 210 as shown in FIG. 20A and performs in the same fashion as the embodiments of the insertion wires described above. That is, in use, the tether 320 can be pulled as indicated by the arrow A in FIG. 20A such that the device (not shown) attached to the opposite end (not shown) of the tether 320 is urged toward the distal end 330 of the overtube 210 until it exits the device lumen 326 of the overtube 210 and is positioned at the procedural site, as depicted in FIG. 20B.

In this implementation as shown in FIGS. 20A and 20B, the tether 320 can be electrical cabling, hydraulic or pneumatic lines, or suction and irrigation lines, any of which can supply further power or actuation to the device 114.

It is understood that in certain embodiments, the overtube is a relatively stiff tube that exhibits some flexibility for facilitating insertion into the patient. In alternative embodiments, the overtube is designed to be stiff enough to provide sufficient rigidity perpendicular to the primary axis of the tube for operation of hydraulics or pneumatic lines. Furthermore, it is understood that positioning the tether in a wire lumen or tether lumen in the overtube helps keep the overtube inner lumen free from tethers, thereby facilitating insertion of various devices through the overtube.

It is understood that many different medical devices, components, and procedures can be used in conjunction with the various device insertion, positioning, and retraction embodiments as shown in FIGS. 13-20B, including the positionable in vivo devices and various robotic devices and procedures described in the various applications incorporated by reference above. That is, the various device insertion, positioning, and retraction embodiments can be used to provide for the insertion, positioning, and/or retraction of one or more medical devices, such that any type of procedure or related device for use in a body cavity can be inserted into, positioned within, and/or retracted from the space, including the various devices and procedures disclosed and incorporated by reference above.

Although the present invention has been described with reference to preferred embodiments, persons skilled in the art will recognize that changes may be made in form and detail without departing from the spirit and scope of the invention.

What is claimed is:

1. A delivery or removal device for delivering or moving a robotic medical device for laparoscopic surgery, the device comprising:
   a. a robotic medical device comprising a first arm and second arm;
   b. an overtube comprising:
      i. an elongate body having a wall, a first end and a second end;
      ii. a device lumen disposed within the body and extending from the first end to the second end; and
      iii. a wire lumen disposed within the wall of the elongate body and extending from the first end to the second end, wherein the device lumen is configured to accommodate the passage of the robotic medical device comprising a first arm and a second arm; and
   c. a retraction wire configured to be disposed within the wire lumen and device lumen so as to urge the robotic medical device comprising a first arm and a second arm through the device lumen.

2. The device of claim 1, wherein the overtube is sized to be positionable through a laparoscopic port or natural orifice.

3. The device of claim 1, wherein the overtube comprises a protrusion at the second end, wherein the protrusion further defines the wire lumen.

4. The device of claim 3, wherein the protrusion further comprises a robotic medical device receiving component configured to receive the robotic medical device.

5. The device of claim 4, wherein the medical device receiving component comprises at least one magnet configured to magnetically couple to the robotic medical device comprising the first arm and second arm, whereby the robotic medical device comprising a first arm and a second arm releasably couples to the medical device receiving component.

6. The device of claim 5, wherein a portion of the protrusion is defined by a portion of a wall of the device lumen.

7. A delivery or removal device, comprising:
   a. a robotic laparoscopic medical device comprising a first arm and second arm;
   b. a tubular body having a proximal end and distal end, the tubular body comprising:
      i. a device lumen defined by the inner surface wall of the tubular body, the device lumen being sized to receive the robotic laparoscopic medical device, the device lumen comprising a proximal device opening at a proximal end of the tubular body and a distal device opening at a distal end of the tubular body; and ii. a wire lumen disposed within the wall of the tubular body, wherein the wire lumen is not coaxial with the device lumen, the wire lumen comprising a proximal wire opening at a proximal end of the tubular body wall and a distal wire opening at a distal end of the tubular body wall, wherein the wire lumen has a smaller diameter than the device lumen; and e. a wire disposed within the wire lumen and device lumen so as to urge the robotic medical device comprising the first arm and second arm through the device lumen.

8. The device of claim 7, wherein the overtube is sized to be positionable through a laparoscopic port or natural orifice.

9. The device of claim 7, wherein the tubular body comprises a protrusion at a distal end of the tubular body, wherein the protrusion further defines the wire lumen.

10. The device of claim 7, wherein the robotic laparoscopic medical device comprising the first arm and second arm further comprises an attachment component disposed on at least one of the first arm or second arm.

11. The device of claim 7, wherein the robotic laparoscopic medical device comprising the first arm and second arm is in vivo device.

12. The device of claim 7, wherein the robotic laparoscopic medical device comprising the first arm and second arm further comprises at least one end effector.

13. The device of claim 12, wherein the at least one end effector is an attachment component.

14. The device of claim 7, wherein the tubular body comprises a protrusion at the distal end, wherein the protrusion further defines the wire lumen.

15. The device of claim 14, wherein the protrusion further comprises a robotic medical device receiving component configured to receive the robotic laparoscopic medical device comprising the first arm and a second arm.

16. The device of claim 15, wherein the medical device receiving component comprises at least one magnet configured to magnetically couple to the robotic medical device comprising the first arm and a second arm, whereby the robotic medical device comprising the first arm and a second arm releasably couples to the medical device receiving component.

17. A delivery or removal device for introducing a robotic laparoscopic medical device comprising a first arm and a second arm into a patient, comprising:

a. a robotic laparoscopic medical device comprising a first arm and a second arm;

b. a tubular body having a proximal end and a distal end and comprising a protrusion at a distal end of the tubular body;

c. a device lumen coextensive with the inner surface of an interior wall of the tubular body, the device lumen being configured to receive the robotic laparoscopic medical device comprising a first arm and a second arm, wherein a portion of the protrusion is defined by a portion of a wall of the device lumen, wherein the device lumen comprises a proximal device opening at a proximal end of the tubular body and a distal device opening at a distal end of the tubular body;

d. a wire lumen disposed within the wall of the tubular body, the wire lumen comprising a proximal wire opening at a proximal end of the tubular body and a distal wire opening at a distal end of the tubular body, wherein the wire lumen has a smaller diameter than the device lumen; and e. a moveable wire disposed through the device lumen and the wire lumen, the moveable wire comprising an attachment component disposed at or near an end of the moveable wire, wherein the attachment component is configured to be removably attachable to the robotic laparoscopic medical device comprising a first arm and a second arm.

18. The device of claim 17, wherein the tubular body is sized to be positionable through a laparoscopic port or natural orifice.

19. The device of claim 17, wherein the robotic laparoscopic medical device comprising the first arm and a second arm is in vivo device.

20. The device of claim 17, wherein the robotic laparoscopic medical device comprising the first arm and a second arm further comprises at least one end effector.

* * * * *